(12) United States Patent
Bennett et al.

(10) Patent No.: US 10,755,816 B2
(45) Date of Patent: *Aug. 25, 2020

(54) CLINICAL DECISION-MAKING ARTIFICIAL INTELLIGENCE OBJECT ORIENTED SYSTEM AND METHOD

(71) Applicants: Indiana University Research and Technology Corporation, Indianapolis, IN (US); Centerstone Research Institute, Bloomington, IN (US)

(72) Inventors: Casey C. Bennett, Bloomington, IN (US); Kris Hauser, Bloomington, IN (US)

(73) Assignees: Indiana University Research and Technology Corporation, Indianapolis, IN (US); Centerstone Research Institute, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/403,683

(22) Filed: May 6, 2019

(65) Prior Publication Data
US 2019/0333636 A1    Oct. 31, 2019

Related U.S. Application Data

(63) Continuation of application No. 14/324,396, filed on Jul. 7, 2014, now Pat. No. 10,282,512.
(Continued)

(51) Int. Cl.
*G16H 20/00* (2018.01)
*G16H 50/00* (2018.01)
*G16H 50/20* (2018.01)

(52) U.S. Cl.
CPC ............. *G16H 50/00* (2018.01); *G16H 50/20* (2018.01)

(58) Field of Classification Search
CPC ...................................................... G16H 20/00
See application file for complete search history.

(56) References Cited

U.S. PATENT DOCUMENTS 6,000,828 A    12/1999  Leet
6,988,088 B1    1/2006  Miikkulainen
(Continued)

OTHER PUBLICATIONS

Patel, Vimla L. et al., The Coming of Age of Artificial Intelligence in Medicine, Artif Intell Med. May 2009 ; 46(1): 18 pages.
(Continued)

*Primary Examiner* — John A Pauls
(74) *Attorney, Agent, or Firm* — Faegre Drinker Biddle & Reath LLP

(57) ABSTRACT

The present invention involves a system and method of providing decision support for assisting medical treatment decision-making. A patient agent software module processes information about a particular patient. A doctor agent software module processes information about a health status of a particular patient, beliefs relating to patient treatments, and the actual effects of treatment decisions. By filtering information over time from the patient agent into the doctor agent, a plurality of decision-outcome nodes are created and formed into a patient-specific outcome tree with the plurality of decision-outcome nodes. An optimal treatment is determined by evaluating the plurality of decision-outcome nodes with a cost per unit change function to output the optimal treatment. When additional information is available from at least one of the patient agent and the doctor agent, the filtering, creating, and determining steps are repeated thus allowing for the system to "reason over time", continuously updating and learning as new information is received.

17 Claims, 8 Drawing Sheets

Related U.S. Application Data

(60) Provisional application No. 61/844,187, filed on Jul. 9, 2013.

(56) References Cited

U.S. PATENT DOCUMENTS

| 7,293,000 | B2* | 11/2007 | Lee | G06N 5/025 706/12 |
|---|---|---|---|---|
| 2004/0073460 | A1 | 4/2004 | Erwin | |

OTHER PUBLICATIONS

McGlynn, Elizabeth A. Ph.D., et al., The Quality of Health Care Delivered to Adults in the United States, New England Journal of Medicine, 348;26, Jun. 26, 2003, pp. 2635-2645.

Baurer, Mark S. MD., A Review of Quantitative Studies of Adherence to Mental Health Clinical Practice Guidelines, Harvard Rev Psychiatry, vol. 10, No. 3, Nov. 8, 2001, pp. 138-153.

Kaplan, Bonnie, Evaluating informatics applications—clinical decision support systems literature review, International Journal of Medical Informatics 64 (2001) pp. 15-37.

Orszag, Roger R. PhD., et al., The Challenge of Rising Health Care Costs—A View from the Congressional Budget Office, New England Journal of Medicine, 357;18, Nov. 1, 2007, pp. 1793-1795.

Purcell, Gretchen et al., How long does it take to train a surgeon?, BMJ: British Medical Journal, vol. 339, No. 7729, Nov. 7, 2009, pp. 1062-1064.

Bennett, Casey M.A., et al., Data Mining and Electronic Health Records: Selecting Optimal Clinical Treatments in Practice, Proceedings of the 6th International Conference on Data Mining, pp. 313-318, http://www.openminds.com/library/110410dmehr.htm.

Osheroff, Jerome A., M.D. et al., A Roadmap for National Action on Clinical Decision Support, American Medical Informatics Association, Jan. 9, 2007, 13 pages.

Bennett, Casey, M.A., et al., Data Mining Session-Based Patient Reported Outcomes (PROs) in a Mental Health Setting: Toward Data-Driven Clinical Decision Support and Personalized Treatment, IEEE Health Informatics and Systems Biology Conference (2011), http://ieeexplore.ieee.org/xpl/freeabs_all.jsp?arnumber=6061404 &abstractAccess=no&userType=, 8 pages.

Kohane, Isaac S., The twin questions of personalized medicine: who are you and whom do you most resemble? Genome Medicine 2009, 1:4, Jan. 20, 2009, 3 pages.

Sun, Yijun, et al., Improved breast cancer prognosis through the combination of clinical and genetic markers, Bioinformatics, vol. 23, No. 1, 2007, pp. 30-37.

Gevaert, Olivier, et al., Predicting the prognosis of breast cancer by integrating clinical and microarray data with Bayesian networks, Bioinformatics, vol. 22, No. 14, 2006, pp. e184-e190.

Boulesteix, Anne-Laure, Microarray-based classification and clinical predictors: On combined classifiers and additional predictive value, Bioinformatics, vol. 00, No. 00, 2005, pp. 1-9.

Beck, J. Robert, M.D., et al., The Markov Process in Medical Prognosis, Med Decis Making, vol. 3, No. 4, 1983, pp. 419-458.

Xiang, Yanping et al., Time-critical dynamic decision modeling in medicine, Computers in Biology and Medicine 32 (2002) pp. 85-97.

Leong, Tze-Yun, Dynamic Decision Modeling in Medicine: A Critique of Existing Formalisms, AMIA, Inc., 1994, pp. 478-484.

Stahl, James E., Modelling Methods for Pharmacoeconomics and Health Technology Assessment, Pharmacoeconomics, 2008, vol. 26, No. 2, pp. 131-148.

Schaefer, Andrew J., et al., 23 Modeling Medical Treatment Using Markov Decision Processes, Department of Industrial Engineering (Pittsburgh, PA), Department of Medicine (Pittsburgh, PA), Center for Research on Health Care University of Pittsburgh (Pittsburgh, PA), date unknown, pp. 599-616.

Alagoz, Oguzhan, PhD., et al, Markov Decision Processes: A Tool for Sequential Decision Making under Uncertainty, Medical Decision Making, Jul.-Aug. 2010, pp. 474-483.

Shechter, Steven M., et al., The Optimal Time to Initiate HIV Therapy under Ordered Health States, Operations Research; Manuscript No. 3, date unknown, 19 pages.

Meehl, Paul E., Causes and Effects of My Disturbing Little Book, Journal of Personality Assessment, 1986, 50(3), pp. 370-375.

Patel, Vimla L., PhD., et al. A Primer on Aspects of Cognition for Medical Informatics, Journal of the American Medical Informatics Association, vol. 8, No. 4, Jul./Aug. 2001, pp. 324-343.

Elstein, Arthur S., et al., Clinical problem solving and diagnostic decision making: selective review of the cognitive literature, BMJ, vol. 324, Mar. 23, 2002, pp. 729-732.

Littman, Michael L., A tutorial on partially observable Markov decision processes, Journal of Mathematical Psychology, vol. 53, No. 3, Jun. 2009, pp. 119-125.

Russell, Stuart J., et al., Artificial Intelligence a Modern Approach, Prentice-Hall, Inc., A Simon & Schuster Company, (1995), 75 pages.

Gocgun, Yasin, et al., A Markov decision process approach to multi-category patient scheduling in a diagnostic facility, date unknown, 21 pages.

Bousquet, F., et al., Multi-agent simulations and ecosystem management: a review, Ecological Modelling, vol. 176, (2004), pp. 313-332.

Miller, Scott D., et al., Using Formal Client Feedback to Improve Retention and Outcome: Making Ongoing, Real-time Assessment Feasible, Journal of Brief Therapy, vol. 5, No. 1, (2006), pp. 5-22.

Campbell, Alistair, et al., Outcome Rating Scale and Session Rating Scale in psychological practice: Clinical utility of ultra-brief measures, Clinical Psychologist, vol. 13, No. 1, Mar. 2009, pp. 1-9.

Bennett, Casey C., Clinical Productivity—A Decision Support Model, International Journal of Productivity and Performance Management. vol. 60, No. 3, 14 pages.

Kreke, Jennifer E., et al., Modeling hospital discharge policies for patients with pneumonia-related sepsis, IIE Transactions, vol. 40, (2008), pp. 853-860.

Ross, Stephane, et al.,Online Planning Algorithms for POMDPs, J Artif Intell Res., vol. 32, No. 2, Jul. 1, 2008, 51 pages.

Goulionis, John E., et al., Medical decision making for patients with Parkinson disease under Average Cost Criterion, Australia and New Zealand Health Policy, BioMedCentral, vol. 6, No. 15, Jun. 24, 2009, 8 pages.

Hauskrecht, Milos, et al., Planning treatment of ischemic heart disease with partially observable Markov decision processes, Artificial Intelligence in Medicine, vol. 18, (2000), pp. 221-244.

Hester, Todd, et al., An Empirical Comparison of Abstraction in Models of Markov Decision Processes, date unknown, 6 pages.

Kim, Minsun, et al., A Markov Decision Process Approach to Temporal Modulation of Dose Fractions in Radiation Therapy Planning, Jan. 20, 2009, 29 pages.

Brown, Matthew, et al., Applying Multi-Agent Techniques to Cancer Modeling, The Sixth Annual Workshop on Multiagent Sequential Decision-Making in Uncertain Domains (MSDM-2011), held in conjunction with AAMAS-2011 on May 3, 2011 in Taipei, Taiwan.

Rosenthal, Meredith B., PhD., Beyond Pay for Performance—Emerging Models of Provider-Payment Reform, New England Journal of Medicine, vol. 359, No. 12, Sep. 18, 2008, pp. 1197-1200.

G.P. Jackson and J.L. Tarpley, How long does it take to train a surgeon? BMJ, (2009) 339: b4260-b4260.

Bennett, Casey C., et al, Artificial Intelligence Framework for Stimulating Clinical Decision Making: A Markov Decision Process Approach. Artificial Intelligence in Medicine. In Press.

* cited by examiner

CLINICAL DECISION-MAKING ARTIFICIAL INTELLIGENCE OBJECT ORIENTED SYSTEM AND METHOD

CROSS-REFERENCE TO RELATED APPLICATIONS

This is a continuation application of U.S. patent application Ser. No. 14/324,396, filed Jul. 7, 2014, which claims priority under 35 U.S.C. § 119 of U.S. Provisional Patent Application Ser. No. 61/844,187, filed Jul. 9, 2013, the disclosures of which are incorporated by reference herein in its entirety.

BACKGROUND OF THE INVENTION

Field of the Invention

The invention relates to decision-making software. More specifically, the present disclosure relates to computational methods, systems, devices and/or apparatuses for clinical medicine decision-making analysis using artificial intelligence type software.

Description of the Related Art

In the modern healthcare system, rapidly expanding costs/complexity, the growing myriad of treatment options, and exploding information streams that often do not effectively reach the front lines hinder the ability to choose optimal treatment decisions over time. Even the answer to the basic healthcare question of "What's wrong with this person" often remains elusive in the modern era—let alone clear answers on the most effective treatment for an individual or how we achieve lower costs and greater efficiency. With the expanding use of electronic health records (EHRs) and growth of large public biomedical datasets (e.g. GenBank, caBig), there is a need to predict optimal treatments, minimize side effects, reduce medical errors/costs, and better integrate research and practice.

Over 1500 Mendelian conditions whose molecular cause is unknown are listed in the Online Mendelian Inheritance in Man (OMIM) database. Additionally, almost all medical conditions are in some way influenced by human genetic variation. The identification of genes associated with these conditions is a goal of numerous research groups, in order to both improve medical care and better understand gene functions, interactions, and pathways. Currently, patients receive correct diagnoses and treatment less than 50% of the time (at first pass). There is stark evidence of a 13-17 year gap between research and practice in clinical care. This reality suggests that the current methods for moving scientific results into actual clinical practice are lacking. Furthermore, evidence-based treatments derived from such research are often out-of-date by the time they reach widespread use and don't always account for real-world variation that typically impedes effective implementation. At the same time, healthcare costs continue to spiral out-of-control, on pace to reach 30% of gross domestic product by 2050 at current growth rates. Training a human doctor to understand/memorize all the complexity of modern healthcare, even in their specialty domain, is a costly and lengthy process—for instance, training a human surgeon now takes on average 10 years or 10,000 hours of intensive involvement.

SUMMARY OF THE INVENTION

The present invention involves computational/artificial intelligence (AI) framework addressing these challenges. First, it provides a simulation environment for understanding and predicting the consequences of various treatment or policy choices. Such simulation modeling helps improve decision-making and the fundamental understanding of the healthcare system and clinical process—its elements, their interactions, and the end result—by playing out numerous potential scenarios in advance. Secondly, such a framework provides the basis for clinical artificial intelligence that can deliberate in advance, form contingency plans to cope with uncertainty, and adjust to changing information on the fly. With careful design and problem formulation, such an AI simulation framework approximates optimal decisions even in complex and uncertain environments, and may approach—and perhaps surpass—human decision-making performance for certain tasks. The success of this framework is shown using real patient data from an EHR.

Combining autonomous AI with human clinicians may serve as the most effective long-term path. Let humans do what they do well, and let machines do what they do well. In the end, the disclosed systems attempt to maximize the potential of both. Such technology functions in multiple roles: enhanced telemedicine services, automated clinician's assistants, and next-generation clinical decision support systems (CDSS).

In one embodiment, autonomous AI software resides within patient monitoring computation devices and within doctor assisting computation devices. Information from such patient monitoring is communicated to the doctor assisting devices and may influence the doctor through a new recommendation or a change in the treatment decisions or beliefs of the doctor. Such AI software then analyzes the effects of these treatment decisions and delivers updated patient-outcome prediction results to the doctor. In another embodiment, such patient monitoring and doctor assisting computation devices function as communication devices to web-based AI software that performs the analysis. Databases of information may be used to help the doctor assisting computation devices, such as electronic health records, personal history records, PACS records, genetic marker records, etc.

In other embodiments of the invention, a method of providing decision support for assisting medical treatment decision-making is implemented. In the method, a patient agent software module processes information about a particular patient and a doctor agent software module for processes information about a health status of a particular patient, beliefs relating to patient treatments, and patent treatment decisions. The method also includes filtering information from the patient agent into the doctor agent to create a plurality of decision-outcome nodes, and creating a patient-specific outcome tree with the plurality of decision-outcome nodes. With the patient-specific outcome tree, an optimal treatment may be determined by evaluating the plurality of decision-outcome nodes with a cost per unit change function and outputting the optimal treatment. Further, when additional information is available from at least one of the patient agent and the doctor agent, repeating the filtering, creating, and determining steps. The cost per unit change function includes calculating the cost in dollars it takes to obtain one unit of outcome change (delta) on a given outcome. The patient agent includes a plurality of health status information at a plurality of times. The doctor agent includes a module that receives rewards/utilities, and a module to select patient treatments in order to maximize overall utilities. The decision-outcome nodes are updated according to a transition model. The method further includes learning wherein when additional information is available, such information is included in a knowledge base used by at least one of the patient agent software module, the doctor agent software module, and in determining optimal treatment.

In another embodiment of the invention, the implementation involves a decision support system for assisting medical treatment decision-making. The system has a processor and associated memory, with program memory configured to store instructions for enabling the processor to perform operations and storage memory configured to store data upon which the processor performs operations. The storage memory includes data relating to a particular patient. The program memory includes a plurality of instructions that when executed by the processor executes software. The patient agent software module is for processing information about a particular patient. The doctor agent software module is for processing information about a health status of a particular patient, beliefs relating to at least one of patient treatments and treatment effects, and effects of patient treatments. The software filters information from the patient agent into the doctor agent to create a plurality of decision-outcome nodes and creates a patient-specific outcome tree with the plurality of decision-outcome nodes. An optimal treatment is determined by evaluating the plurality of decision-outcome nodes with a cost per unit change function and outputting the optimal treatment. The optimal treatment is reevaluated when additional information is available from at least one of the patient agent and the doctor agent, after updating the patient-specific outcome tree. The cost per unit change function includes calculating the cost in dollars it takes to obtain one unit of outcome change (delta) on a given outcome. The patient agent includes a plurality of health status information at a plurality of times. The doctor agent includes a module to receive rewards/utilities, and a module to select patient treatments in order to maximize overall utilities. The decision-outcome nodes are updated according to a transition model. A further learning software module has a knowledge base wherein when additional information is available, such information is included in the knowledge base which is used by at least one of the patient agent software module, the doctor agent software module, and the determining optimal treatment step.

A further embodiment of the present invention involves a server for providing decision support for medical treatment decision-making. The system comprises a processor and associated memory, the memory including program memory configured to store instructions for enabling the processor to perform operations. The memory also includes storage memory configured to store data upon which the processor performs operations. The storage memory includes data relating to a particular patient, and the program memory includes a plurality of instructions that when executed by the processor enables the processor to execute computer program steps. For example, receiving evidence based information about a health status of a particular patient, doctor beliefs relating to at least one of patient treatments and treatment effects, and patient treatment decisions; filtering the evidence based information to create a plurality of decision-outcome nodes; and determining an optimal treatment by evaluating the plurality of decision-outcome nodes with a scoring function and outputting a message including the optimal treatment.

Such predictive software systems have a variety of possible uses. In one embodiment, such software systems may be centered around a particular patient, so that the attending physician has addition decision support information with which to formulate a diagnosis and treatment plan. In another embodiment, such software systems may be centered around a particular type or class of health conditions and/or treatments so that a population of patients may be monitored and general treatment options for the target population may be discerned. In further embodiments, such software systems may be used with payment or reimbursement systems to allocate resources, e.g. government or insurance payors. Each of these embodiments may also be implemented as a server operating by receiving and sending information and messages relating to the aforementioned uses.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein.

Figure 1:
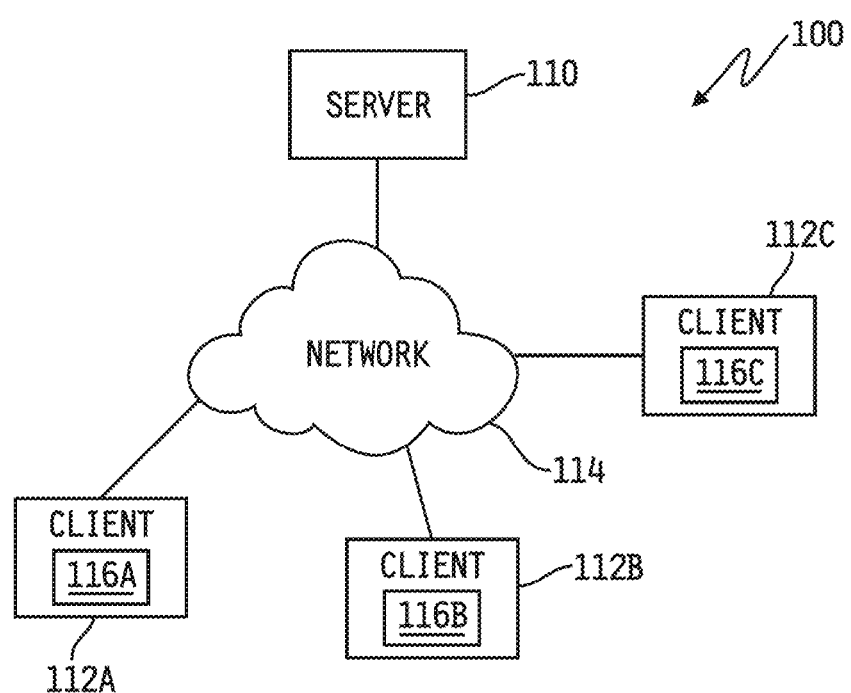
FIG. 1 is a schematic diagrammatic view of a network system in which embodiments of the present invention may be utilized.

Corresponding reference characters indicate corresponding parts throughout the several views. Although the drawings represent embodiments of the present invention, the drawings are not necessarily to scale and certain features may be exaggerated in order to better illustrate and explain the present invention. The flow charts and screen shots are also representative in nature, and actual embodiments of the invention may include further features or steps not shown in the drawings. The exemplification set out herein illustrates an embodiment of the invention, in one form, and such exemplifications are not to be construed as limiting the scope of the invention in any manner.

DESCRIPTION OF THE PRESENT INVENTION

The embodiment disclosed below is not intended to be exhaustive or limit the invention to the precise form disclosed in the following detailed description. Rather, the embodiment is chosen and described so that others skilled in the art may utilize its teachings.

Computational approaches for determining optimal treatment decisions at single timepoints via the use of data mining/machine learning techniques have been the subject of earlier research, for example in [7] C. C. Bennett and T. W. Doub, Data mining and electronic health records: Selecting optimal clinical treatments in practice, Proceedings of the 6th International Conference on Data Mining, (CSREA Press, Las Vegas, Nev., 2010) 313-318; and [9] C. C. Bennett, T. W. Doub, A. D. Bragg, J. Luellen, C. Van Regenmorter, J. Lockman, et al., Data Mining Session-Based Patient Reported Outcomes (PROs) in a Mental Health Setting: Toward Data-Driven Clinical Decision Support and Personalized Treatment, IEEE Health Informatics, Imaging, and Systems Biology Conference, (IEEE, San Jose, Calif., 2011) 229-236, the disclosures of which are explicitly incorporated by reference herein. Initial results of such approaches have achieved success rates of near 80% in predicting optimal treatment for individual patients with complex, chronic illness, and hold promise for further improvement. Predictive algorithms based on such data-driven models are essentially an individualized form of practice-based evidence drawn from the live population. Another term for this is "personalized medicine."

The ability to adapt specific treatments to fit the characteristics of an individual's disorder transcends the traditional disease model. Prior work in this area has primarily addressed the utility of genetic data to inform individualized care. However, it is likely that the next decade will see the integration of multiple sources of data—genetic, clinical, socio-demographic—to build a more complete profile of the individual, their inherited risks, and the environmental/behavioral factors associated with disorder and the effective treatment thereof. Indeed, a trend is emerging of combining clinical and genetic indicators in prediction of cancer prognosis as a way of developing cheaper, more effective prognostic tools, for example as disclosed in Sun Y, S. Goodison S, J. Li, L. Liu, and W. Farmerie, Improved breast cancer prognosis through the combination of clinical and genetic markers, Bioinformatics, (2007) 23(1): 30-37; O. Gevaert, F. De Smet, D. Timmerman, Y. Moreau, and B, De Moor, Predicting the prognosis of breast cancer by integrating clinical and microarray data with Bayesian networks, Bioinformatics, (2006) 22(14):184-190; and A. L. Boulesteix, C. Porzelius, and M. Daumer, Microarray-based classification and clinical predictors: on combined classifiers and additional predictive value, Bioinformatics, (2008) 24(15): 1698-1706, the disclosures of which are incorporated by reference herein.

Such computational approaches can serve as a component of a larger potential framework for real-time data-driven clinical decision support, or "adaptive decision support." This framework can be integrated into an existing clinical workflow, essentially functioning as a form of artificial intelligence that "lives" within the clinical system, can "learn" over time, and can adapt to the variation seen in the actual real-world population. The approach is two-pronged—both developing new knowledge about effective clinical practices as well as modifying existing knowledge and evidence-based models to fit real-world settings.

Embodiments of the invention extend these approaches beyond optimizing treatments at single decision points in clinical settings. Embodiments of the invention consider sequential decision processes, in which a sequence of inter-related decisions must be made over time, such as those encountered in the treatment of chronic disorders.

Modeling of dynamic sequential decision-making in medicine involves several techniques. Among these modeling techniques are Markov-based approaches, originally described in terms of medical decision-making by J. R. Beck and S. G. Pauker, The Markov process in medical prognosis, Med Decis Making, (1983) 3(4):419-58, the disclosures of which are incorporated by reference herein. Other approaches utilize dynamic influence diagrams or decision trees to model temporal decisions, see Y. Xiang and K. L. Poh, Time-critical dynamic decision modeling in medicine, Comput Biol Med, (2002) 32(2): 85-97; T. Y. Leong, Dynamic decision modeling in medicine: a critique of existing formalisms., Proc Annu Symp Comput Appl Med Care, (AMIA, Washington, D.C., 1993) 478-484; and J. E. Stahl, Modelling methods for pharmacoeconomics and health technology assessment: an overview and guide, Pharmacoeconomics, (2008) 26(2): 131-48, the disclosures of which are incorporated by reference herein. A general overview of simulation modeling techniques disclosed in Stahl 2008. In all cases, the goal is to determine optimal sequences of decisions out to some horizon. The treatment of time—whether it is continuous or discrete, and (if the latter) how time units are determined—is a critical aspect in any modeling effort, as are the trade-offs between solution quality and solution time. Problems may be either finite-horizon or infinite-horizon. In either case, utilities/rewards of various decisions may be undiscounted or discounted, where discounting increases the importance of short-term utilities/rewards over long-term ones, see A. J. Schaefer, M. D. Bailey, S. M. Shechter, and M. S. Roberts, Modeling Medical Treatment Using Markov Decision Processes, in: M. L. Brandeau, F. Sainfort, and W. P. Pierskalla, eds., Operations Research and Health Care, (Kluwer Academic Publishers, Boston, 2005) 593-612, the disclosures of which are incorporated by reference herein.

Markov decision processes (MDPs) are one efficient technique for determining such optimal sequential decisions (termed a "policy") in dynamic and uncertain environments, for example in 0. Alagoz, H. Hsu, A. J. Schaefer, and M. S. Roberts, Markov Decision Processes: A Tool for Sequential Decision Making under Uncertainty, Med Decis Making, (2010) 30(4): 474-83, the disclosures of which are incorporated by reference herein, and have been explored in specific medical decision-making problems, for example in S. M. Shechter, M. D. Bailey, A. J. Schaefer, and M. S. Roberts, The Optimal Time to Initiate HIV Therapy Under Ordered Health States, Oper Res, (2008) 56(1): 20-33, the disclosures of which are incorporated by reference herein. MDPs (and their partially observable cousins) directly address many of the challenges faced in clinical decision-making. Clinicians typically determine the course of treatment considering current health status as well as some internal approximation of the outcome of possible future treatment decisions. However, the effect of treatment for a given patient is non-deterministic (i.e. uncertain), and attempting to predict the effects of a series of treatments over time only compounds this uncertainty. A Markov approach provides a principled, efficient method to perform probabilistic inference over time given such non-deterministic action effects. Other complexities (and/or sources of uncertainty) include limited resources, unpredictable patient behavior (e.g., lack of medication adherence), and variable treatment response time. These sources of uncertainty may be directly modeled as probabilistic components in a Markov model. Additionally, the use of outcome deltas, averse to clinical outcomes themselves, may provide a convenient history meta-variable for maintaining the central Markov assumption: that the state at time t depends only on the information at time t−1. Currently, most treatment decisions in the medical domain are made via ad-hoc or heuristic approaches, but there is a growing body of evidence that such complex treatment decisions are better handled through modeling rather than intuition alone, for example in P. E. Meehl, Causes and effects of my disturbing little book, Journal of Personality Assessment, (1986) 50(3): 370-375, the disclosures of which are incorporated by reference herein.

Partially observable Markov decision processes (POMDPs) extend MDPs by maintaining internal belief states about patient status, treatment effect, etc., similar to the cognitive planning aspects in a human clinician, see V. L. Patel, J. F. Arocha, and D. R. Kaufman, A Primer on Aspects of Cognition for Medical Informatics, J Am Med Inform Assoc, (2001) 8(4): 324-43; and A. S. Elstein and A. Schwarz, Clinical problem solving and diagnostic decision making: selective review of the cognitive literature, BMJ, (2002) 324(7339): 729-32, the disclosures of which are incorporated by reference herein. This helps deal with real-world clinical issues of noisy observations and missing data (e.g. no observation at a given timepoint). By using temporal belief states, POMDPs may account for the probabilistic relationship between observations and underlying health status over time and reason/predict even when observations are missing, while still using existing methods to perform efficient Bayesian inference. MDPs/POMDPs may also be designed as online AI agents—determining an optimal policy at each timepoint (t), taking an action based on that optimal policy, then re-determining the optimal policy at the next timepoint (t+1) based on new information and/or the observed effects of performed actions, for example as disclosed in M. L. Littman, A tutorial on partially observable Markov decision processes, J Math Psycho], (2009) 53(3): 119-25; and S. Russell and P. Norvig, Artificial Intelligence: A Modern Approach, 3rd Ed, (Prentice Hall, Upper Saddle River, N J, 2010), the disclosures of which are incorporated by reference herein.

A challenge in applying MDP/POMDPs is that they involve a data-intensive estimation step to generate reasonable transition models—how belief states evolve over time—and observation models—how unobserved variables affect observed quantities. Large state/decision spaces are also computationally expensive to solve particularly in the partially observable setting, and must adhere to specific Markov assumptions that the current timepoint (t) is dependent only on the previous timepoint (t−1). Careful formulation of the problem and state space is necessary to handle such issues.

Embodiments of the invention involve MDP/POMDP simulation framework using agents based on clinical EHR data drawn from real patients in a chronic care setting. Optimization of "clinical utility" is done in terms of cost-effectiveness of treatment (utilizing both outcomes and costs) while accurately reflecting realistic clinical decision-making. The focus is on the physician's (or physician agent's) optimization of treatment decisions over time. The results of these computational approaches are compared with existing treatment-as-usual approaches to demonstrate the viability of the AI framework which approaches or even surpasses human decision-making performance.

The framework of embodiments of the invention is structured as a multi-agent system (MAS) for future potential studies, and combining MDPs and MAS opens up many interesting opportunities. For instance, systems may model personalized treatment simply by having each patient agent maintain their own individualized transition model. MAS may capture the sometimes synergistic, sometimes conflicting nature of various components of such systems and exhibit emergent, complex behavior from simple interacting agents, see in another context F. Bousquet and C. Le Page, Multi-agent simulations and ecosystem management: a review, Ecol Modell, (2004) 176(3-4): 31332, the disclosures of which are incorporated by reference herein. For instance, a physician may prescribe a medication, but the patient may not adhere to treatment.

In the field of molecular biology, gene expression profiling is the measurement of the activity (the expression) of thousands of genes at once, to create a global picture of cellular function including protein and other cellular building blocks. These profiles may, for example, distinguish between cells that are actively dividing or otherwise reacting to the current bodily condition, or show how the cells react to a particular treatment such as positive drug reactions or toxicity reactions. Many experiments of this sort measure an entire genome simultaneously, that is, every gene present in a particular cell, as well as other important cellular building blocks.

DNA Microarray technology measures the relative activity of previously identified target genes. Sequence based techniques, like serial analysis of gene expression (SAGE, SuperSAGE) are also used for gene expression profiling. SuperSAGE is especially accurate and may measure any active gene, not just a predefined set. The advent of next-generation sequencing has made sequence based expression analysis an increasingly popular, "digital" alternative to microarrays called RNA-Seq.

Expression profiling provides a view to what a patient's genetic materials are actually doing at a point in time. Genes contain the instructions for making messenger RNA (mRNA), but at any moment each cell makes mRNA from only a fraction of the genes it carries. If a gene is used to produce mRNA, it is considered "on", otherwise "off". Many factors determine whether a gene is on or off, such as the time of day, whether or not the cell is actively dividing, its local environment, and chemical signals from other cells. For instance, skin cells, liver cells and nerve cells turn on (express) somewhat different genes and that is in large part what makes them different. Therefore, an expression profile allows one to deduce a cell's type, state, environment, and so forth.

Expression profiling experiments often involve measuring the relative amount of mRNA expressed in two or more experimental conditions. For example, genetic databases have been created that reflect a normative state of a healthy patient, which may be contrasted with databases that have been created from a set of patient's with a particular disease or other condition. This contrast is relevant because altered levels of a specific sequence of mRNA suggest a changed need for the protein coded for by the mRNA, perhaps indicating a homeostatic response or a pathological condition. For example, higher levels of mRNA coding for one particular disease is indicative that the cells or tissues under study are responding to the effects of the particular disease. Similarly, if certain cells, for example a type of cancer cells, express higher levels of mRNA associated with a particular transmembrane receptor than normal cells do, the expression of that receptor is indicative of cancer. A drug that interferes with this receptor may prevent or treat that type of cancer. In developing a drug, gene expression profiling may assess a particular drug's toxicity, for example by detecting changing levels in the expression of certain genes that constitute a biomarker of drug metabolism.

For a type of cell, the group of genes and other cellular materials whose combined expression pattern is uniquely characteristic to a given condition or disease constitutes the gene signature of this condition or disease. Ideally, the gene signature is used to detect a specific state of a condition or disease to facilitates selection of treatments. Gene Set Enrichment Analysis (GSEA) and similar methods take advantage of this kind of logic and uses more sophisticated statistics. Component genes in real processes display more complex behavior than simply expressing as a group, and the amount and variety of gene expression is meaningful. In any case, these statistics measure how different the behavior of some small set of genes is compared to genes not in that small set.

One way to analyze sets of genes and other cellular materials apparent in gene expression measurement is through the use of pathway models and network models. Many protein-protein interactions (PPIs) in a cell form protein interaction networks (PINs) where proteins are nodes and their interactions are edges. There are dozens of PPI detection methods to identify such interactions. In addition, gene regulatory networks (DNA-protein interaction networks) model the activity of genes which is regulated by transcription factors, proteins that typically bind to DNA. Most transcription factors bind to multiple binding sites in a genome. As a result, all cells have complex gene regulatory networks which may be combined with PPIs to link together these various connections. The chemical compounds of a living cell are connected by biochemical reactions which convert one compound into another. The reactions are catalyzed by enzymes. Thus, all compounds in a cell are parts of an intricate biochemical network of reactions which is called the metabolic network, which may further enhance PPI and/or DNA-protein network models. Further, signals are transduced within cells or in between cells and thus form complex signaling networks that may further augment such genetic interaction networks. For instance, in the MAPK/ERK pathway is transduced from the cell surface to the cell nucleus by a series of protein-protein interactions, phosphorylation reactions, and other events. Signaling networks typically integrate protein-protein interaction networks, gene regulatory networks, and metabolic networks.

The detailed descriptions which follow are presented in part in terms of algorithms and symbolic representations of operations on data bits within a computer memory representing genetic profiling information derived from patient sample data and populated into network models. A computer generally includes a processor for executing instructions and memory for storing instructions and data. When a general purpose computer has a series of machine encoded instructions stored in its memory, the computer operating on such encoded instructions may become a specific type of machine, namely a computer particularly configured to perform the operations embodied by the series of instructions. Some of the instructions may be adapted to produce signals that control operation of other machines and thus may operate through those control signals to transform materials far removed from the computer itself. These descriptions and representations are the means used by those skilled in the art of data processing arts to most effectively convey the substance of their work to others skilled in the art.

An algorithm is here, and generally, conceived to be a self-consistent sequence of steps leading to a desired result. These steps are those requiring physical manipulations of physical quantities. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as bits, values, symbols, characters, display data, terms, numbers, or the like as a reference to the physical items or manifestations in which such signals are embodied or expressed. It should be borne in mind, however, that all of these and similar terms are to be associated with the appropriate physical quantities and are merely used here as convenient labels applied to these quantities.

Some algorithms may use data structures for both inputting information and producing the desired result. Data structures greatly facilitate data management by data processing systems, and are not accessible except through sophisticated software systems. Data structures are not the information content of a memory, rather they represent specific electronic structural elements which impart or manifest a physical organization on the information stored in memory. More than mere abstraction, the data structures are specific electrical or magnetic structural elements in memory which simultaneously represent complex data accurately, often data modeling physical characteristics of related items, and provide increased efficiency in computer operation.

Further, the manipulations performed are often referred to in terms, such as comparing or adding, commonly associated with mental operations performed by a human operator. No such capability of a human operator is necessary, or desirable in most cases, in any of the operations described herein which form part of the present invention; the operations are machine operations. Useful machines for performing the operations of the present invention include general purpose digital computers or other similar devices. In all cases the distinction between the method operations in operating a computer and the method of computation itself should be recognized. The present invention relates to a method and apparatus for operating a computer in processing electrical or other (e.g., mechanical, chemical) physical signals to generate other desired physical manifestations or signals. The computer operates on software modules, which are collections of signals stored on a media that represents a series of machine instructions that enable the computer processor to perform the machine instructions that implement the algorithmic steps. Such machine instructions may be the actual computer code the processor interprets to implement the instructions, or alternatively may be a higher level coding of the instructions that is interpreted to obtain the actual computer code. The software module may also include a hardware component, wherein some aspects of the algorithm are performed by the circuitry itself rather as a result of an instruction.

The present invention also relates to an apparatus for performing these operations. This apparatus may be specifically constructed for the required purposes or it may comprise a general purpose computer as selectively activated or reconfigured by a computer program stored in the computer. The algorithms presented herein are not inherently related to any particular computer or other apparatus unless explicitly indicated as requiring particular hardware. In some cases, the computer programs may communicate or relate to other programs or equipments through signals configured to particular protocols which may or may not require specific hardware or programming to interact. In particular, various general purpose machines may be used with programs written in accordance with the teachings herein, or it may prove more convenient to construct more specialized apparatus to perform the required method steps. The required structure for a variety of these machines will appear from the description below.

The present invention may deal with "object-oriented" software, and particularly with an "object-oriented" operating system. The "object-oriented" software is organized into "objects", each comprising a block of computer instructions describing various procedures ("methods") to be performed in response to "messages" sent to the object or "events" which occur with the object. Such operations include, for example, the manipulation of variables, the activation of an object by an external event, and the transmission of one or more messages to other objects.

Messages are sent and received between objects having certain functions and knowledge to carry out processes. Messages are generated in response to user instructions, for example, by a user activating an icon with a "mouse" pointer generating an event. Also, messages may be generated by an object in response to the receipt of a message. When one of the objects receives a message, the object carries out an operation (a message procedure) corresponding to the message and, if necessary, returns a result of the operation. Each object has a region where internal states (instance variables) of the object itself are stored and where the other objects are not allowed to access. One feature of the object-oriented system is inheritance. For example, an object for drawing a "circle" on a display may inherit functions and knowledge from another object for drawing a "shape" on a display.

A programmer "programs" in an object-oriented programming language by writing individual blocks of code each of which creates an object by defining its methods. A collection of such objects adapted to communicate with one another by means of messages comprises an object-oriented program. Object-oriented computer programming facilitates the modeling of interactive systems in that each component of the system can be modeled with an object, the behavior of each component being simulated by the methods of its corresponding object, and the interactions between components being simulated by messages transmitted between objects.

An operator may stimulate a collection of interrelated objects comprising an object-oriented program by sending a message to one of the objects. The receipt of the message may cause the object to respond by carrying out predetermined functions which may include sending additional messages to one or more other objects. The other objects may in turn carry out additional functions in response to the messages they receive, including sending still more messages. In this manner, sequences of message and response may continue indefinitely or may come to an end when all messages have been responded to and no new messages are being sent. When modeling systems utilizing an object-oriented language, a programmer need only think in terms of how each component of a modeled system responds to a stimulus and not in terms of the sequence of operations to be performed in response to some stimulus. Such sequence of operations naturally flows out of the interactions between the objects in response to the stimulus and need not be preordained by the programmer.

Although object-oriented programming makes simulation of systems of interrelated components more intuitive, the operation of an object-oriented program is often difficult to understand because the sequence of operations carried out by an object-oriented program is usually not immediately apparent from a software listing as in the case for sequentially organized programs. Nor is it easy to determine how an object-oriented program works through observation of the readily apparent manifestations of its operation. Most of the operations carried out by a computer in response to a program are "invisible" to an observer since only a relatively few steps in a program typically produce an observable computer output.

In the following description, several terms which are used frequently have specialized meanings in the present context. The term "object" relates to a set of computer instructions and associated data which can be activated directly or indirectly by the user. The terms "windowing environment", "running in windows", and "object oriented operating system" are used to denote a computer user interface in which information is manipulated and displayed on a video display such as within bounded regions on a raster scanned video display. The terms "network", "local area network", "LAN", "wide area network", or "WAN" mean two or more computers which are connected in such a manner that messages may be transmitted between the computers. In such computer networks, typically one or more computers operate as a "server", a computer with large storage devices such as hard disk drives and communication hardware to operate peripheral devices such as printers or modems. Other computers, termed "workstations", provide a user interface so that users of computer networks can access the network resources, such as shared data files, common peripheral devices, and inter-workstation communication. Users activate computer programs or network resources to create "processes" which include both the general operation of the computer program along with specific operating characteristics determined by input variables and its environment. Similar to a process is an agent (sometimes called an intelligent agent), which is a process that gathers information or performs some other service without user intervention and on some regular schedule. Typically, an agent, using parameters typically provided by the user, searches locations either on the host machine or at some other point on a network, gathers the information relevant to the purpose of the agent, and presents it to the user on a periodic basis.

The term "desktop" means a specific user interface which presents a menu or display of objects with associated settings for the user associated with the desktop. When the desktop accesses a network resource, which typically requires an application program to execute on the remote server, the desktop calls an Application Program Interface, or "API", to allow the user to provide commands to the network resource and observe any output. The term "Browser" refers to a program which is not necessarily apparent to the user, but which is responsible for transmitting messages between the desktop and the network server and for displaying and interacting with the network user. Browsers are designed to utilize a communications protocol for transmission of text and graphic information over a world wide network of computers, namely the "World Wide Web" or simply the "Web". Examples of Browsers compatible with the present invention include the Internet Explorer program sold by Microsoft Corporation (Internet Explorer is a trademark of Microsoft Corporation), the Opera Browser program created by Opera Software ASA, or the Firefox browser program distributed by the Mozilla Foundation (Firefox is a registered trademark of the Mozilla Foundation). Although the following description details such operations in terms of a graphic user interface of a Browser, the present invention may be practiced with text based interfaces, or even with voice or visually activated interfaces, that have many of the functions of a graphic based Browser.

Browsers display information which is formatted in a Standard Generalized Markup Language ("SGML") or a HyperText Markup Language ("HTML"), both being scripting languages which embed non-visual codes in a text document through the use of special ASCII text codes. Files in these formats may be easily transmitted across computer networks, including global information networks like the Internet, and allow the Browsers to display text, images, and play audio and video recordings. The Web utilizes these data file formats to conjunction with its communication protocol to transmit such information between servers and workstations. Browsers may also be programmed to display information provided in an eXtensible Markup Language ("XML") file, with XML files being capable of use with several Document Type Definitions ("DTD") and thus more general in nature than SGML or HTML. The XML file may be analogized to an object, as the data and the stylesheet formatting are separately contained (formatting may be thought of as methods of displaying information, thus an XML file has data and an associated method).

The terms "personal digital assistant" or "PDA", as defined above, means any handheld, mobile device that combines computing, telephone, fax, e-mail and networking features. The terms "wireless wide area network" or "WWAN" mean a wireless network that serves as the medium for the transmission of data between a handheld device and a computer. The term "synchronization" means the exchanging of information between a first device, e.g. a handheld device, and a second device, e.g. a desktop computer, either via wires or wirelessly. Synchronization ensures that the data on both devices are identical (at least at the time of synchronization).

In wireless wide area networks, communication primarily occurs through the transmission of radio signals over analog, digital cellular or personal communications service ("PCS") networks. Signals may also be transmitted through microwaves and other electromagnetic waves. At the present time, most wireless data communication takes place across cellular systems using second generation technology such as code-division multiple access ("CDMA"), time division multiple access ("TDMA"), the Global System for Mobile Communications ("GSM"), Third Generation (wideband or "3G"), Fourth Generation (broadband or "4G"), personal digital cellular ("PDC"), or through packet-data technology over analog systems such as cellular digital packet data ("CDPD") used on the Advance Mobile Phone Service ("AMPS").

The terms "wireless application protocol" or "WAP" mean a universal specification to facilitate the delivery and presentation of web-based data on handheld and mobile devices with small user interfaces. "Mobile Software" refers to the software operating system which allows for application programs to be implemented on a mobile device such as a mobile telephone or PDA. Examples of Mobile Software are Java and Java ME (Java and JavaME are trademarks of Sun Microsystems, Inc. of Santa Clara, Calif.), BREW (BREW is a registered trademark of Qualcomm Incorporated of San Diego, Calif.), Windows Mobile (Windows is a registered trademark of Microsoft Corporation of Redmond, Wash.), Palm OS (Palm is a registered trademark of Palm, Inc. of Sunnyvale, Calif.), Symbian OS (Symbian is a registered trademark of Symbian Software Limited Corporation of London, United Kingdom), ANDROID OS (ANDROID is a registered trademark of Google, Inc. of Mountain View, Calif.), and iPhone OS (iPhone is a registered trademark of Apple, Inc. of Cupertino, Calif.), and Windows Phone 7. "Mobile Apps" refers to software programs written for execution with Mobile Software.

"PACS" refers to Picture Archiving and Communication System (PACS) involving medical imaging technology for storage of, and convenient access to, images from multiple source machine types. Electronic images and reports are transmitted digitally via PACS; this eliminates the need to manually file, retrieve, or transport film jackets. The universal format for PACS image storage and transfer is DICOM (Digital Imaging and Communications in Medicine). Non-image data, such as scanned documents, may be incorporated using consumer industry standard formats like PDF (Portable Document Format), once encapsulated in DICOM. A PACS typically consists of four major components: imaging modalities such as X-ray computed tomography (CT) and magnetic resonance imaging (MRI) (although other modalities such as ultrasound (US), positron emission tomography (PET), endoscopy (ES), mammograms (MG), Digital radiography (DR), computed radiography (CR), etc. may be included), a secured network for the transmission of patient information, workstations and mobile devices for interpreting and reviewing images, and archives for the storage and retrieval of images and reports. When used in a more generic sense, PACS may refer to any image storage and retrieval system.

FIG. 1 is a high-level block diagram of a computing environment 100 according to one embodiment. FIG. 1 illustrates server 110 and three clients 112 connected to network 114. Only three clients 112 are shown in FIG. 1 in order to simplify and clarify the description. Embodiments of the computing environment 100 may have thousands or millions of clients 112 connected to network 114, for example the Internet. Users (not shown) may operate software 116 on one of clients 112 to both send and receive messages network 114 via server 110 and its associated communications equipment and software (not shown).

Figure 2:
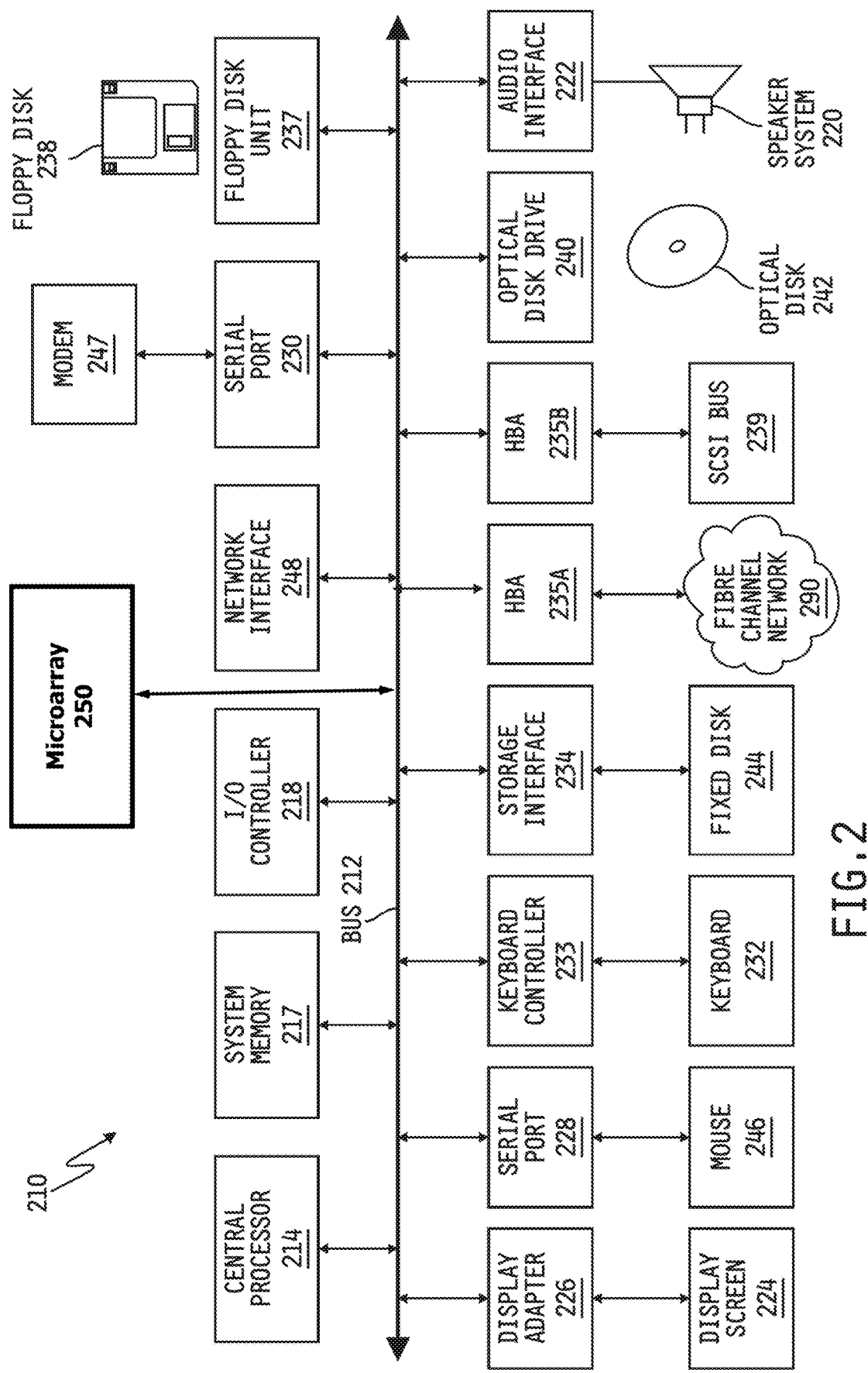
FIG. 2 is a block diagram of a computing system (either a server or client, or both, as appropriate), with optional input devices (e.g., keyboard, mouse, touch screen, etc.) and output devices, hardware, network connections, one or more processors, and memory/storage for data and modules, etc. which may be utilized in conjunction with embodiments of the present invention.

FIG. 2 depicts a block diagram of computer system 210 suitable for implementing server 110 or client 112. Computer system 210 includes bus 212 which interconnects major subsystems of computer system 210, such as central processor 214, system memory 217 (typically RAM, but which may also include ROM, flash RAM, or the like), input/output controller 218, external audio device, such as speaker system 220 via audio output interface 222, external device, such as display screen 224 via display adapter 226, serial ports 228 and 230, keyboard 232 (interfaced with keyboard controller 233), storage interface 234, disk drive 237 operative to receive floppy disk 238, host bus adapter (HBA) interface card 235A operative to connect with Fibre Channel network 290, host bus adapter (HBA) interface card 235B operative to connect to SCSI bus 239, and optical disk drive 240 operative to receive optical disk 242. Also included are mouse 246 (or other point-and-click device, coupled to bus 212 via serial port 228), modem 247 (coupled to bus 212 via serial port 230), and network interface 248 (coupled directly to bus 212).

Bus 212 allows data communication between central processor 214 and system memory 217, which may include read-only memory (ROM) or flash memory (neither shown), and random access memory (RAM) (not shown), as previously noted. RAM is generally the main memory into which operating system and application programs are loaded. ROM or flash memory may contain, among other software code, Basic Input-Output system (BIOS) which controls basic hardware operation such as interaction with peripheral components. Applications resident with computer system 210 are generally stored on and accessed via computer readable media, such as hard disk drives (e.g., fixed disk 244), optical drives (e.g., optical drive 240), floppy disk unit 237, or other storage medium. Additionally, applications may be in the form of electronic signals modulated in accordance with the application and data communication technology when accessed via network modem 247 or interface 248 or other telecommunications equipment (not shown).

Storage interface 234, as with other storage interfaces of computer system 210, may connect to standard computer readable media for storage and/or retrieval of information, such as fixed disk drive 244. Fixed disk drive 244 may be part of computer system 210 or may be separate and accessed through other interface systems. Modem 247 may provide direct connection to remote servers via telephone link or the Internet via an internet service provider (ISP) (not shown). Network interface 248 may provide direct connection to remote servers via direct network link to the Internet via a POP (point of presence). Network interface 248 may provide such connection using wireless techniques, including digital cellular telephone connection, Cellular Digital Packet Data (CDPD) connection, digital satellite data connection or the like.

Many other devices or subsystems (not shown) may be connected in a similar manner (e.g., document scanners, digital cameras and so on). Conversely, all of the devices shown in FIG. 2 need not be present to practice the present disclosure. Devices and subsystems may be interconnected in different ways from that shown in FIG. 2. Operation of a computer system such as that shown in FIG. 2 is readily known in the art and is not discussed in detail in this application. Software source and/or object codes to implement the present disclosure may be stored in computer-readable storage media such as one or more of system memory 217, fixed disk 244, optical disk 242, or floppy disk 238. The operating system provided on computer system 210 may be a variety or version of either MS-DOS® (MS-DOS is a registered trademark of Microsoft Corporation of Redmond, Wash.), WINDOWS® (WINDOWS is a registered trademark of Microsoft Corporation of Redmond, Wash.), OS/2® (OS/2 is a registered trademark of International Business Machines Corporation of Armonk, N.Y.), UNIX® (UNIX is a registered trademark of X/Open Company Limited of Reading, United Kingdom), Linux® (Linux is a registered trademark of Linus Torvalds of Portland, Oreg.), or other known or developed operating system. In some embodiments, computer system 210 may take the form of a tablet computer, typically in the form of a large display screen operated by touching the screen. In tablet computer alternative embodiments, the operating system may be iOS® (iOS is a registered trademark of Cisco Systems, Inc. of San Jose, Calif., used under license by Apple Corporation of Cupertino, Calif.), Android® (Android is a trademark of Google Inc. of Mountain View, Calif.), Blackberry® Tablet OS (Blackberry is a registered trademark of Research In Motion of Waterloo, Ontario, Canada), webOS (webOS is a trademark of Hewlett-Packard Development Company, L.P. of Texas), and/or other suitable tablet operating systems.

Moreover, regarding the signals described herein, those skilled in the art recognize that a signal may be directly transmitted from a first block to a second block, or a signal may be modified (e.g., amplified, attenuated, delayed, latched, buffered, inverted, filtered, or otherwise modified) between blocks. Although the signals of the above described embodiments are characterized as transmitted from one block to the next, other embodiments of the present disclosure may include modified signals in place of such directly transmitted signals as long as the informational and/or functional aspect of the signal is transmitted between blocks. To some extent, a signal input at a second block may be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

One peripheral device particularly useful with embodiments of the present invention is microarray 250. Generally, microarray 250 represents one or more devices capable of analyzing and providing genetic expression and other molecular information from patients. Microarrays may be manufactured in different ways, depending on the number of probes under examination, costs, customization requirements, and the type of analysis contemplated. Such arrays may have as few as 10 probes or over a million micrometre-scale probes, and are generally available from multiple commercial vendors. Each probe in a particular array is responsive to one or more genes, gene-expressions, proteins, enzymes, metabolites and/or other molecular materials, collectively referred to hereinafter as targets or target products.

In some embodiments, gene expression values from microarray experiments may be represented as heat maps to visualize the result of data analysis. In other embodiments, the gene expression values are mapped into a network structure and compared to other network structures, e.g. normalized samples and/or samples of patients with a particular condition or disease. In either circumstance, a simple patient sample may be analyzed and compared multiple times to focus or differentiate diagnoses or treatments. Thus, a patient having signs of multiple conditions or diseases may have microarray sample data analyzed several times to clarify possible diagnoses or treatments.

It is also possible, in several embodiments, to have multiple types of microarrays, each type having sensitivity to particular expressions and/or other molecular materials, and thus particularized for a predetermined set of targets. This allows for an iterative process of patient sampling, analysis, and further sampling and analysis to refine and personalize diagnoses and treatments for individuals. While each commercial vendor may have particular platforms and data formats, most if not all may be reduced to standardized formats. Further, sample data may be subject to statistical treatment for analysis and/or accuracy and precision so that individual patient data is a relevant as possible. Such individual data may be compared to large databases having thousands or millions sets of comparative data to assist in the experiment, and several such databases are available in data warehouses and available to the public. Due to the biological complexity of gene expression, the considerations of experimental design are necessary so that statistically and biologically valid conclusions may be drawn from the data.

Microarray data sets are commonly very large, and analytical precision is influenced by a number of variables. Statistical challenges include taking into account effects of background noise and appropriate normalization of the data. Normalization methods may be suited to specific platforms and, in the case of commercial platforms, some analysis may be proprietary. The relation between a probe and the mRNA that it is expected to detect is not trivial. Some mRNAs may cross-hybridize probes in the array that are supposed to detect another mRNA. In addition, mRNAs may experience amplification bias that is sequence or molecule-specific. Thirdly, probes that are designed to detect the mRNA of a particular gene may be relying on genomic Expression Sequence Tag (EST) information that is incorrectly associated with that gene.

A general framework overview is provided in FIG. 3, which is further elaborated below. The agents (shown in double-line borders) encapsulate the characteristics and functions of their respective real-life counterparts—e.g. patient agents incorporate individual patient-specific data and individualized transition models while physician agents maintain beliefs about patients' health status and treatment effects and have decision-making capabilities. The types of agents (Physician, Patient) are shown in double-line borders, and represent one or more such agents. The other boxes represent various aspects of the model. When viewed as a linear process, the general flow is: phase 1) create patient-specific MDPs/physician agent filters evidence into existing beliefs, phase 2) recurse through MDP search tree to determine optimal action, and phase 3) perform treatment action and update belief states. Alternatively, when viewed as a dynamic process, when new information is received in one part of the framework, then new information is cascaded through the items related to the new information until information dependent on the new information is accordingly updated, wherein the decided optimal action is the latest actual action until new information is received somewhere in the framework.

Figure 3:
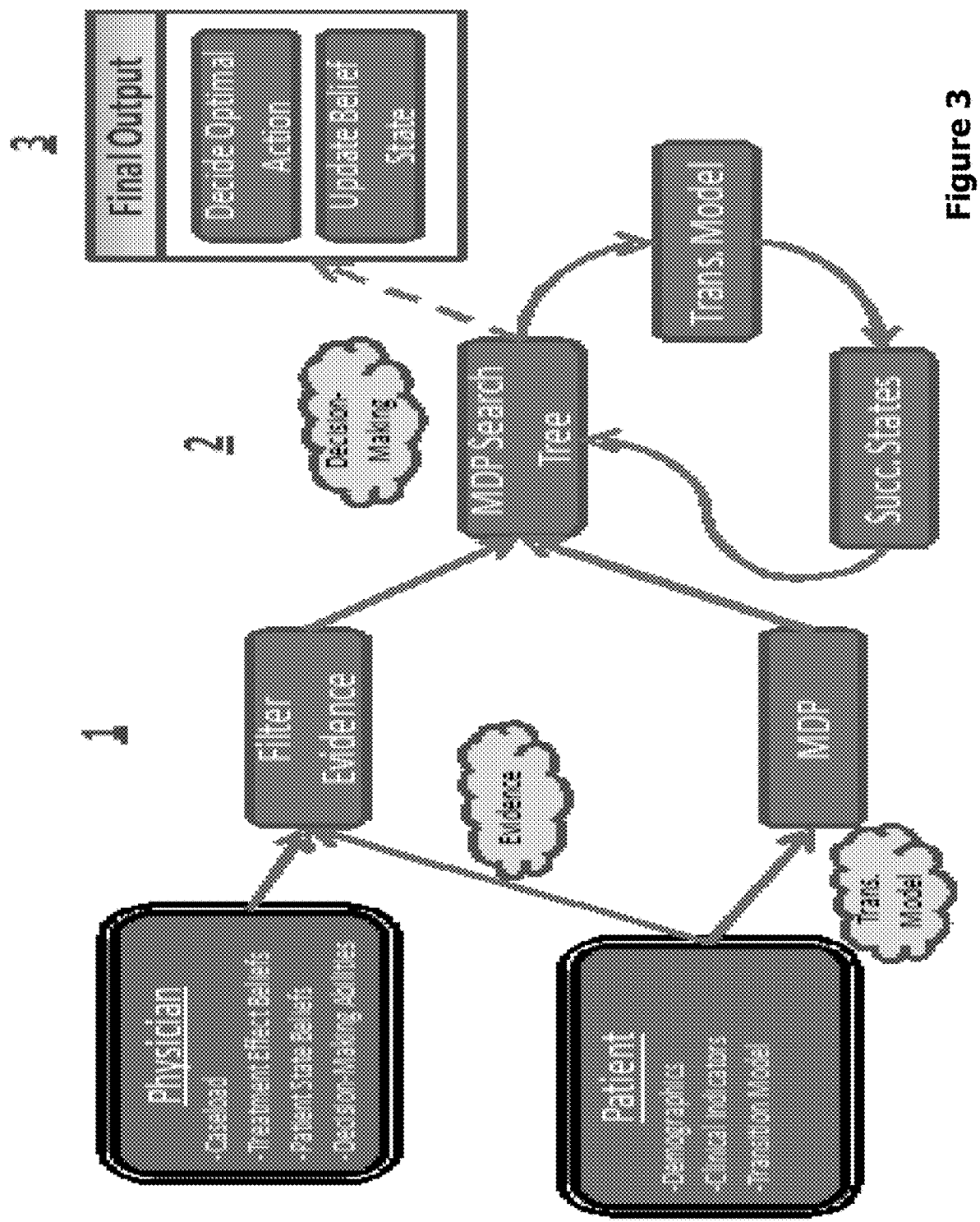
FIG. 3 is a schematic process flow diagram illustrating one embodiment of the decision support system of the present invention.

FIG. 3 also displays the general algorithm (which in an exemplary embodiment is implemented using Python 2.7, see www.python.org), where initially patient-specific MDPs are created from the transition models and physician agents incorporate patient-specific evidence/information into existing beliefs prior to decision-making at each timepoint. The decision-making process then recurses down the MDP search tree, resulting finally in a determination of an optimal current action and updates to patient belief states. The algorithm steps are as follows: (1) Create patient and physician agents; (2) Create patient-specific MDP then, for each timepoint (while not horizon): (3) Calculate current outcome delta, physician agent filters evidence; (4) Determine optimal current action via MDP search tree; (5) Perform action and update belief states; and (6) If action does not equal "do not treat," then return to step (3).

The decision-making environment may be modeled as a finite-horizon, undiscounted, sequential decision-making process in which the state st from the state space S consists of a patient's health status at time t. At each time step the physician agent makes a decision to treat or stop treatment (an action at from the binary action space A=10,11). Here time corresponds to the number of treatment sessions since the patient's first visit (typically one session=one week). The physician agent receives rewards/utilities, and is asked to pick actions in order to maximize overall utilities. Similar decision-making models were used in references [19,31,32]. In one exemplary embodiment, this decision is modeled as a dynamic decision network (DDN, a type of dynamic Bayesian network), as seen in FIG. 4.

Figure 4:
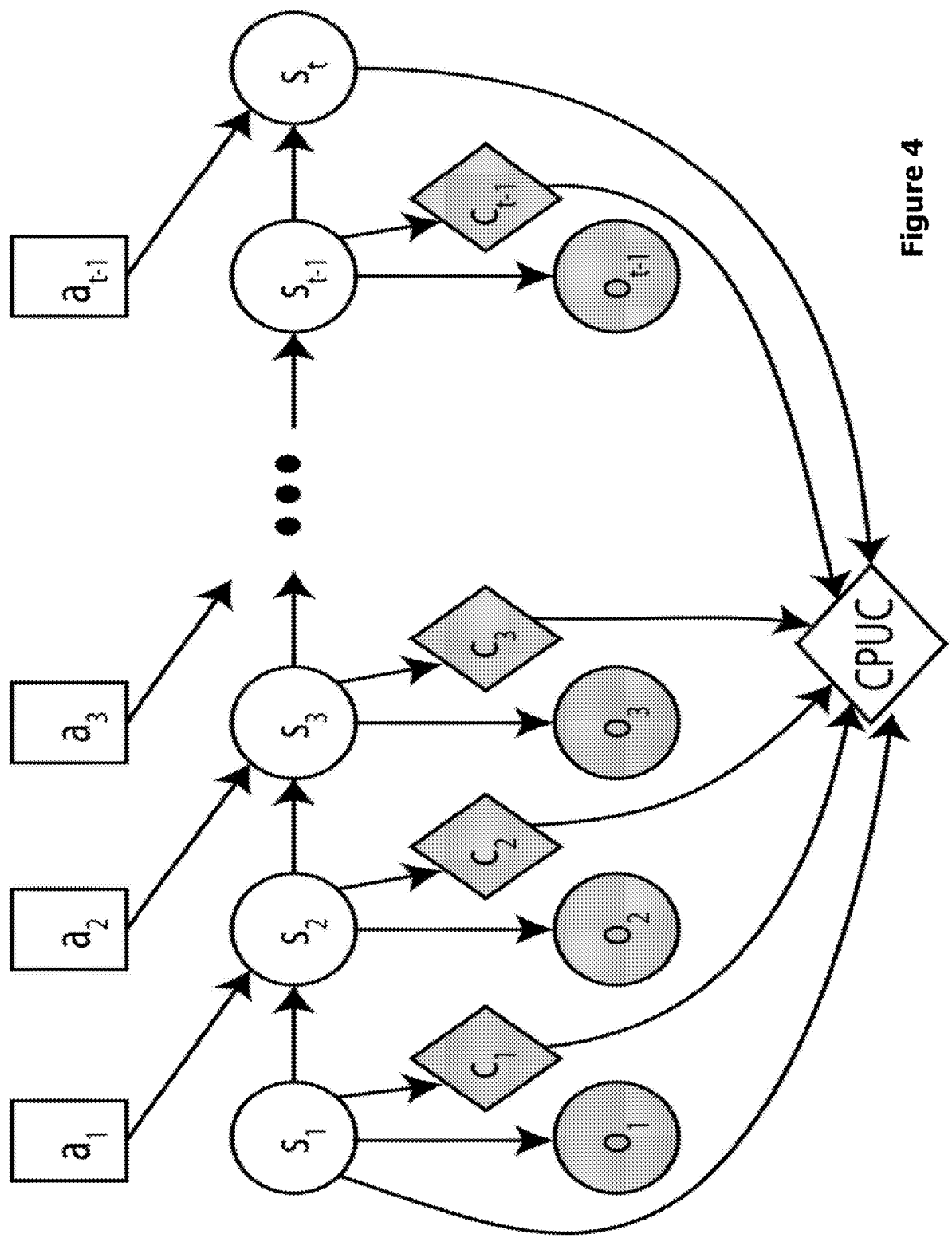
FIG. 4 is a node diagram representing the operation of various agents according to another embodiment of the present invention.

In FIG. 4, the graphic depicts a dynamic decision network for clinical decision-making, with the following types of nodes: a=action (e.g. treatment option, or not treat), s=state (patient's actual underlying health status, not directly observable), o=observation (patient's observed status/outcome, may be missing), c=treatment costs, CPUC=utilities/rewards (cost per unit change of some outcome measure). The subscripts represent time slices (e.g. treatment sessions).

In terms of decision-making analysis, we are interested in the following: at time t, what is the optimal action (a) to choose? The answer depends on what the agent has observed so far, the beliefs the agent has inferred from those observations, and what the agent expects might happen in the future.

In one of several embodiments of the invention, health status is taken to be the delta value (change over time) of the CDOI-ORS ("Client-Directed Outcome-Informed"-" Outcome Rating Scale", or ACDOI), given an observation at time t, but more generally state models may represent underlying characteristics of disease, clinical/demographic characteristics, and individual genetic predispositions. States—actual, st, and belief states, bt (see below)—are derived by discretizing continuous CDOI delta values into five discrete bins: High Deterioration (ACDOI<-4), Low Deterioration (-4<=ACDOI<-1), Flatline/Stable (-1<=ACDOI<=1), Low Improvement (1<ACDOI<=4) and High Improvement (ACDOI>4). These bins are derived from research-validated clinical categorization of significant outcome delta classes for CDOI-ORS, for example, as described by Miller et al. in reference 28. This binning is helpful for computational tractability. While the following description describes embodiments using the CDOI outcome, any outcome variable may be used for the Outcome Rating Scale, for example without limitation blood glucose readings, blood pressure, cancer metastatis stage, etc. In several embodiments, the outcome of interest is measured by amount of change, or deltas, which has the advantage of being essentially scale-free and can work directly with many numerical outcome measures. Alternatively, a scaled outcome measure may be used, which may then require an appropriate adjusting scalar in further computations relating to the outcome measure.

The effects of actions on the state may be modeled using a transition model (T R) that encodes the probabilistic effects of various treatment actions:

$$TR(S_{t+1}, S_t, a_t) = P(s_{t+1} | s_t, a_t)$$

which is assumed stationary (invariant to the time step).

The physician agent's performance objective is often to maximize the improvement in patient health, as measured by the change in CDOI-ORS score at the end of treatment, while minimizing cost of treatment (e.g. by stopping treatment when the probability of further improvement is low), to maximize the utility of the physician's performance. Utility function calculations may also have other associated metrics with an associated numerical scoring function. These two competing objectives are combined via the cost per unit change (CPUC) metric that incorporates both outcome delta (change over time) and treatment costs. Treatment strategies with low CPUC are cost effective (i.e., have a high utility function score). An optimal strategy 7C" that minimizes CPUC is given as:

$$\pi^* = \arg\min CPUC(\pi)$$

$$= \arg\min_\pi E \begin{cases} \frac{C_T(\pi)}{\Delta CDOI(\pi)} & \text{if } \Delta CDOI(\pi) \geq 1 \\ \frac{C_T(\pi)}{1} + (1 - \Delta CDOI(\pi)) \times CPS & \text{else} \end{cases}$$

where CPS=cost per service for a given session, CT is a random variable denoting accumulated cost at the end of treatment, E indicates expected value (since we are calculating over future events), and ACDOI(π) is calculated as:

$$\Delta CDOI(\pi) = CDOI_T(\pi) - CDOI_0$$

where CDOIT is a random variable denoting the CDOI-ORS value at the end of treatment. The expectation is taken over future patient health trajectories up to a finite horizon T, here taken to be T=8 treatments (based on the typical average number of sessions amongst one exemplary outpatient population, used in one embodiment of the invention). In cases where the CDOI delta<=0, we rescale the delta values so that as a utility metric, given equal costs, delta=0 is effectively one unit worse than delta=1, delta=−1 is one unit worse than delta=0, and so on. This is done by adding additional costs to the CPUC for delta=1.

In all cases, the treatment decision is based on the belief state rather than the true underlying state (which cannot be directly observed)—that is, a strategy 7C is defined as a map from belief states to actions: $\pi:2^s$ A. In other words, the physician agent's reasoning is performed in a space of belief states, which are probability distributions over the patient's health status, $b_t(s)=P(s_t=s)$. For instance, we cannot directly observe a patient's disease state (e.g. diabetes); rather, we take measurements of symptoms (e.g. blood glucose) and attempt to classify the patient into some underlying disease or health state. Furthermore, in approximately 30% of our data, the clinician makes a treatment decision when the CDOI-ORS observation is missing (i.e. partially observable environment), and the belief state must be inferred from previous belief states (see below). The belief state categories are the same as those described above for the true underlying state (High Deterioration, Flatline, etc.) The determination of the treatment decision may be extended to reason optimally when integrating unobserved health factors based on their probabilistic relationship to observed clinical/demographic characteristics, as well as account for non-deterministic effects of variable treatment options.

Unconditional on observations, the next belief state, $b_t+i$, is predicted from the prior belief (over all possible prior states) using the following exact equation:

$$b_{t+1}(s_{t+1}) = \text{predict } (b_t, a_t) = \sum_{st} TR(s_{t+1}, s_t, a_t) b_t(s_t)$$

By repeated application of this predict operation embodiments of the invention may compute forecasts of the patient's health status into the future.

Over time, uncertainty of the belief state is reduced by relating the observations that are actually seen by the physician to the health status; in other words, when observations are available, we utilize them to update the belief states. In this embodiment of the invention, observations of are drawn from the observation space 0={missing} u CDOI. In the case of a missing observation, $o_t$={missing}, the belief $b_t(s)$ is maintained as is after the observation. This provides a probabilistic observation model, which defines the relationship between the true underlying state and possible observations:

$$O(o_t,s_t)=P(o_t|s_t)$$

Upon receiving an observation of $o_t$, we find the posterior belief over the patient's state using the update operation, which uses Bayes rule to derive the backward relationship from an observation to the state distribution:

$$b_{t|o_t}(S) = \text{Update } (b_t, o_t) = \frac{1}{Z} \times P(o_t|S) b_t(S)$$

where Z is a normalization factor equal to the unconditional probability of observing ot. For all patients and their current belief state, the physician agent maintains a continuous-valued estimate of CDOI-ORS at the given timepoint by applying a Gaussian model of average treatment effect (estimated from the EHR data) to the CDOI-ORS value at the previous timepoint given the predicted belief state, $b_t(s)$ (e.g. High Improvement). This continuous-valued CDOI-ORS belief may be recalculated as a delta and then re-binned into states for future prediction steps, $b_t+r(s)$.

The goal of the transition model is to use the history of health status—i.e. outcome delta—to predict the probability distribution of future health states on the subsequent time step. Let ht denote the history of observations (o1, . . . , ot). We compare three model classes for predicting the change in CDOI-ORS from the current to the next step: ΔCDOIt=CDOIt+1−CDOIt. 1) 0th order—a raw stationary distribution over ΔCDOIt independent of history (i.e. the probability of treatment effect, regardless of improvement/deterioration seen thus far): P(ΔCDOIt ht)=P(ΔCDOIt); 2) 1st order autoregressive (Local)—the distribution over ΔCDOIt depends only on change since the previous timepoint (local change): P(ΔCDOIt ht)=P(ΔCDOIt ΔCDOIt−1); 3) Global average—the distribution over ΔCDOIt depends on the entire patient history (i.e. delta since baseline): P(ΔCDOIt I ht)=P(ΔCDOIt I (CDOIt−CDOI0)).

The 0th order model ignores any effect of the history on future patient outcomes and treats each patient like a new average patient regardless of previous observations. For instance, even if the patient has already experienced significant outcome improvement, the 0th order model still assumes they are just as likely to improve in the future. On the other hand, the 1st order local model uses the short-term trajectory of prior improvement/deterioration in order to gain somewhat better forecasting ability, but only since the most recent timepoint (previous treatment session). One potential drawback of this method is that it may be fooled by large and/or spurious short-term oscillations in patient outcomes. The global averaging technique looks at trends over a longer time horizon (change since baseline, t=0). It provides the most comprehensive measure but is less sensitive to recent changes, which may be significant for real-world treatment decisions. The global technique also maintains the Markov property required for MDP use by capturing the total history of outcome change as a state meta-variable of a given timepoint. Models of differing orders may further be combined to improve forecasting (e.g. 1st order/local and global deltas).

For each transition model class, we build a discrete conditional probability table over the values of the independent variable using observed statistics from our EHR data (in other words, using a separate sample of patients from the EHR, we estimate the transition probabilities needed for the model). To obtain sufficient sample size for the estimation procedure, we bin deltas into 5 bins (High Deterioration, Low Deterioration, Flatline/Stable, Low improvement, High Improvement) based on research-validated clinical categories. For each model, we estimated transition probabilities using maximum likelihood from EHR data. As typical for many EHR systems, our dataset only contains CDOI-ORS data for patients to the point of treatment termination—i.e., we have no information on patients' health status after the discontinuation of services. As noted elsewhere, the collection of such "natural history" disease data is fraught with many challenges, ethical and otherwise, particularly if such untreated conditions pose significant health risks. Hence, we make the coarse approximation that untreated individuals, on average, remain roughly constant at ΔCDOIt=0.

EXAMPLES

Clinical data, including outcomes, treatment information, demographic information, and other clinical indicators, was obtained from the electronic health record (EHR) at Centerstone Research Institute ("Centerstone") for 961 patients who participated in the Client-Directed Outcome-Informed (CDOI) pilot study in 20] 0, as well as patients who participated in the ongoing evaluation of CDOI post-pilot phase. This sample contained 5,807 patients, primarily consisting of major clinical depression diagnoses, with a significant number of patients (~65%) exhibiting co-occurring chronic physical disorders including hypertension, diabetes, chronic pain, and cardiovascular disease. Centerstone healthcare providers in Tennessee and Indiana see over 75,000 distinct patients a year across over 130 outpatient clinical sites. Centerstone has a fully-functional system-wide EHR that maintains virtually all relevant patient records.

In all simulations, 500 randomly selected patients were used. All other aspects, probabilities, and parameters for modeling were estimated directly from the EHR data (e.g. average cost per service, expected values of outcome improvement and deterioration, and transition model probabilities).

In all subsequent simulations, a single physician agent with a caseload of 500 randomly selected patients was used. This embodiment of the framework handles multiple physician agents, but in this simulation there are no variable behaviors across physicians (e.g. variable attitudes towards outcome significance, where one physician pays a lot of attention to outcome observations and another does not). The physician agent makes a treatment decision for each patient at each timepoint over the course of seven sessions (plus baseline/intake, max total sessions=8).

The primary outcome of interest used in these examples is the Outcome Rating Scale (ORS) component of the CDOI assessment, which is a validated ultra-brief measure of functioning and symptomology for chronic and acute mental disorders, with over a decade of research supporting its use in similar settings and populations. The ORS correlates highly with lengthier, traditional outcome measures such as 0Q-45 and the Quality of Life Scale (QOLS), see A. Campbell and S. Hemsley, Outcome Rating Scale and Session Rating Scale in psychological practice: Clinical utility of ultra-brief measures, Clinical Psychologist, (2009) 13(1): 1-9, the disclosures of which are incorporated by reference herein. The ORS has been shown previously to be useful as the basis for machine learning algorithms to predict individualized patient treatment response.

The utility metric, which is used to evaluate the quality of decisions in a model, is cost per unit change (CPUC), which measures the cost in dollars it takes to obtain one unit of outcome change (delta) on a given outcome, as disclosed in C.C. Bennett, Clinical Productivity System: A Decision Support Model, International Journal of Productivity and Performance Management, (2010) 60(3): 311-319, the disclosures of which are incorporated by reference herein. CPUC is used as a relative measure of cost-effectiveness of treatment, given as a ratio between costs and outcome change. In this study, CPUC was calculated using the change in CDOI-ORS over time (delta)—the delta calculation varying dependent on the formulation of the transition model. However, CPUC may alternatively be calculated for any disease and/or outcome measure—e.g. blood pressure, cancer metastasis stage, hospitalization days, quality-adjusted life years (QALYs). Hence, the use of CPUC, rather than directly using outcomes, for utility/rewards in the modeling framework is principle to keeping the model general purpose (non-disease-specific).

To determine optimal actions via the DDN, we compute an optimal treatment strategy via exploration of a belief-space search tree (MDP search tree). Here, we present an online approach where the system continually plans, executes, observes, and re-plans the optimal treatment strategy from any given timepoint.

Figure 5:
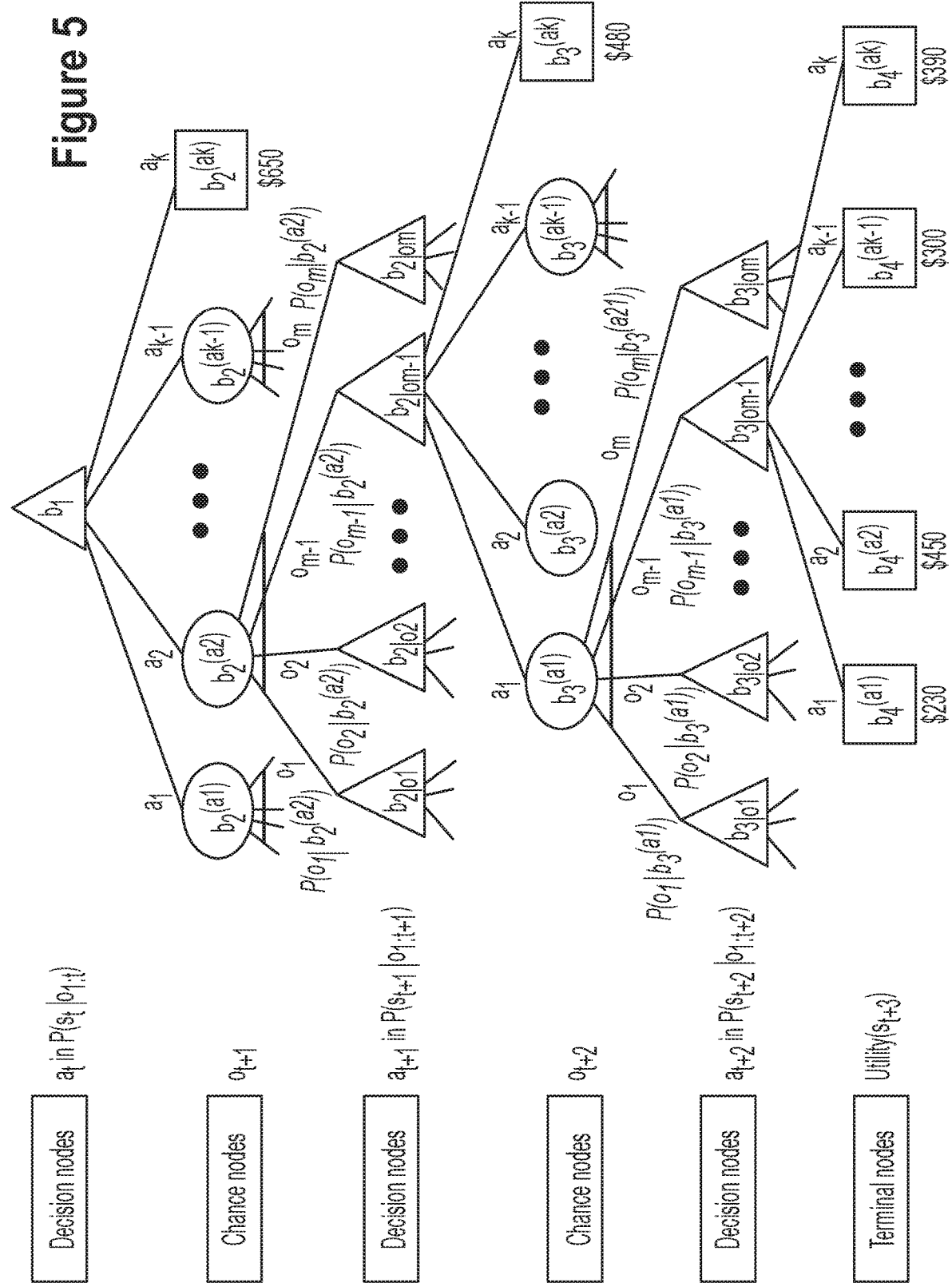
FIG. 5 is a search tree diagram representing a simulation calculation process according to a further embodiment of the present invention.

The MDP/POMDP search tree, also sometimes referred to as a stochastic decision tree, explores the beliefs (b) obtained for all possible actions (a) and probabilistic treatment outcomes (observations, o) out into the future (FIG. 5). The tree alternates layers of decision nodes—in which the physician agent has a choice of action—and chance nodes—in which the environment (including other agents' actions, non-deterministic treatment effects, and so on) yields uncertain changes to the patient health status. For stop-treatment actions, we also construct terminal nodes. In our case, we end enumerating layers at the finite horizon, T=8 (producing a tree of depth 16 in total).

FIG. 5 shows an exemplary MDP search tree for clinical decision-making, with nodes relating to decision-outcome results. At each layer/time slice, we have a series of decision and chance (or terminal) nodes. Decision nodes represent choices of actions (a, given k possible actions), while chance nodes represent possible resulting observations (o, given m possible observations). Terminal nodes present a utility measure (CPUC, represented in dollars). As none of these actions or observations has occurred yet, we must use probabilistic beliefs (b) at each planning step.

We then make a backwards pass to compute the optimal decisions at each decision node that optimizes CPUC. The first step in this pass computes the overall CPUC at leaves and terminal nodes. Then, we recursively backup the optimal CPUC for interior nodes all the way to the root. The backup operation for chance nodes calculates the expected CPUC over its children (based on probabilities), while at decision nodes the backup picks the action that leads to the optimal (in this case, minimal) CPUC for its subtree. Once this operation is complete, we may compute the optimal strategy. The optimal strategy is a subtree obtained by keeping all children of chance nodes and the single child corresponding to the optimal action at each decision node. This optimal strategy represents a treatment plan given current information. Where the various branches, b, can relate to possible observations, o=1 ol . . . oml, at the decision nodes and actions, a={al . . . ak}, at the probabilistic nodes. Each node contains some utility value (here a CPUC value shown in dollars).

One challenge in this approach is exploring the large search tree that may result. Here, we consider 5 observation bins and a "stop treatment" action with no subsequent branches, resulting in a search tree with branching factor=5 and depth=10 and the generation of over 100,000 belief states in the worst case. While tractable for the problem at hand, more complex decision problems—such as larger state spaces, action types, or time frames—may require approximate solutions.

For comparative purposes with the MDP models, we evaluated several simpler decision-making approaches. These alternative strategies provide context for interpreting the optimality of the MDP results.

We considered two heuristic policies that represent current healthcare models. The MDP models were constructed only with the 1st order and global transition models, as the MDP policy is trivial in the 0th order case because ACDOI from t to t−F1 is assumed independent of prior history. As such, the 0th order models essentially represent their own decision-making approach—henceforth referred to as Raw Effect models, given they consider the raw effect of treatment without consideration of outcome change history. Given its optimistic nature, the Raw Effect model results in always treating till the horizon. The Raw Effect model provides an upper baseline, which represents the overly-optimistic scenario of assuming treatment always results in patient improvement. This is, in effect, an approximation of the fee-for-service model prevalent in U.S healthcare. We also considered a Hard Stop policy after the third treatment session. The Hard Stop strategy provides a lower baseline, simulating the worst-case scenario of simply stopping treatment after some arbitrary timepoint without consideration for outcomes (minimizing costs). This is, in effect, an approximation of the case-rate/capacitated model used by many insurance companies.

Additionally, for the 1st order and global transition models, we consider two simpler decision-making approaches (that do consider outcome change history): 1) Max Improve that assumes the treatment effect of maximum probability always occurs for a given action (This could be considered a "winner-take-all" approach); and 2) Probabilistic models select an action at random, where the action is chosen with probability proportional to its likelihood to improve CDOI. For example, if treatment was predicted to improve CDOI with probability 0.9, then the strategy would flip a biased coin with probability 0.9 to decide whether to treat.

Both of the above models—as well as the Raw Effect model—only consider the probabilities of treatment effects for a given action from t to t+1, unlike the MDP approach which calculates utilities of a current action across multiple future timepoints considering possible action sequences, treatment effects, and contingency plans. We consider them here to evaluate whether the added complexity of the MDP models results in justifiable performance improvement in a healthcare setting.

For purposes of analysis, simulation experiments were performed across multiple permutations of the transition and decision-making models laid out above (henceforth termed constructs). We also considered datasets with and without missing observation points.

Additionally, for the MDP model solved via DDN/search tree, the significance of the outcomes was varied via an outcome scaling factor (OSF) that adds in scaled outcome values 0-1 as an additional component of the utility metric. The outcomes (current delta) are scaled and flipped based on the maximum possible delta for a patient at a given timepoint (delta.), so that higher values (near 1) are worse than lower values (given that we are attempting to minimize CPUC):

$$CPUC_{Final} = CPUC + OSF \times \left(\frac{delta_{max} - delta}{delta_{max}}\right)$$

Although any scaling to the range y={0-1} and flipped so that OSF=1−y would work. Increasing this OSF above 0 increases the added importance of outcomes in the decision-making process. It should be noted—this is "added" influence, because outcomes are already accounted for in the basic CPUC reward/utility calculation, even when this factor is set to 0. When set to 0, outcomes are considered equally important as costs.

For the probabilistic decision-making models, it was necessary to perform multiple runs (n=10) of each construct in order to build a statistical sample from which to derive mean values for CPUC, outcomes, etc. given these probabilistic models are purely non-deterministic nature. For the other decision-making models, this was unnecessary.

Figure 7:
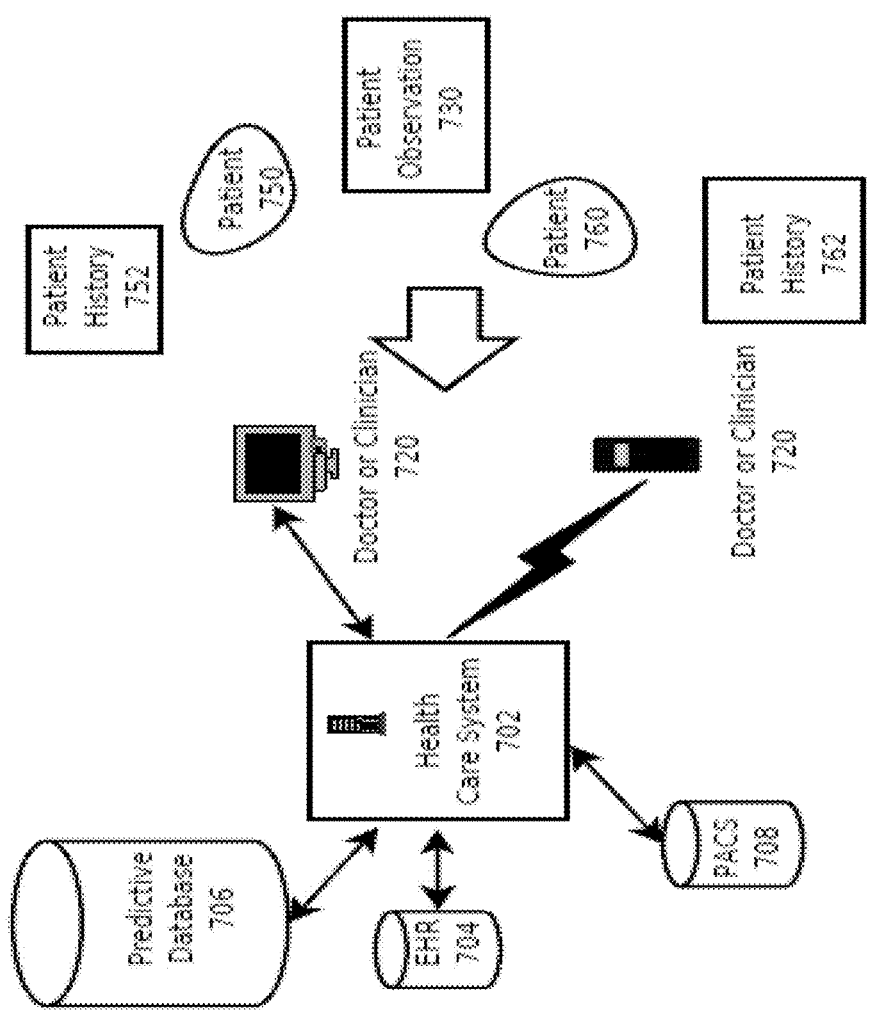
FIG. 7 is a schematic diagrammatic view of a healthcare system focused embodiment of the present invention.
Figure 8:
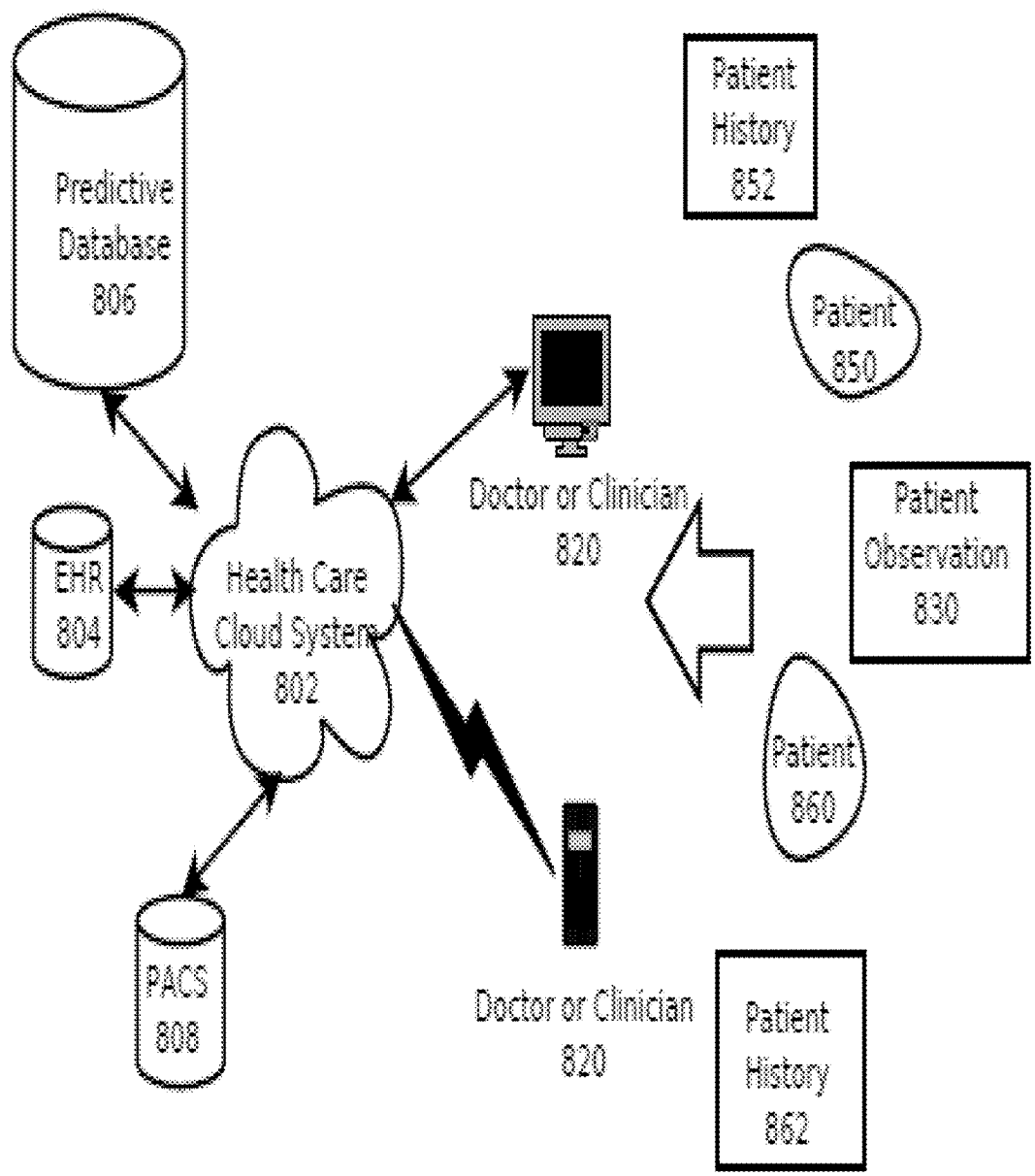
FIG. 8 is a schematic diagrammatic view of a cloud based embodiment of the present invention.

FIGS. 7 and 8 illustrate two exemplary embodiments of a computer based system of the present invention. FIG. 7 is focused on Health Care System 702, which has data collections from several sources including, but not limited to, Electronic Health Record (EHR) database 704 (representing a collection of patient specific information), PACS database 708 (representing a collection of patient specific images and related observed information), and predictive database 706 (representing a collection of population statistics such as disease indications or genetic tendencies). Other sources of information may also be useful to the above described methods and processes, and may be captured in a central location such as Health Care System 702, for example from Patient History 752 or 762, Patient Observation 730 (representing devices that monitor and provide patient data, including but not limited to pulse from a suitable sensor, blood pressure from a suitable sensor, brain wave from a suitable sensor, blood testing from a suitable sensor or a lab report, genetic testing from a micro-array or lab report, etc.), and observations from doctors or other clinicians 720 taken by a computer, tablet, smart phone, etc. Finally, Patient 750 or 760 may provide data in the form of prior or current measurements, personal feelings or observations, or other historical evidence. In some embodiments, the information is strictly numeric and processed accordingly, while in other embodiments the information may be coded or in a natural language. In other embodiments, a portion of the information is numeric in character while in another portion of the information is coded or in a natural language.

Similarly in FIG. 8, Health Care Cloud System 702 may provide access to EHR 804, PACS 808, or Predictive Database 806, and doctor or clinician 820 may access such data through a personal computer, tablet, smart phone, etc., through Cloud system 820, and additional information from Patient History 852 and 862, Patient Observation 830, and/or Patient 850 or 860 may be similarly communicated. In addition to the embodiments shown in FIGS. 7 and 8, hybrid systems may be employed where patient data partially resides in a fixed location (such as Health Care System 702) and other patient data resides in the cloud (such as in Health Care Cloud System 802). The agents of the above examples may, in some embodiments, execute on local machines using the local data (for example on a clinician's tablet computer with down loaded data). In other embodiments, such agents may execute on remote devices (for example in Health Care System 702 or Health Care Cloud System 802), with the results being displayed on a local device. Numerous embodiments are possible with various arrangements of local and remote data and local and remote computing to deliver the decision support assistance of the present invention.

Example Data

Nearly 100 different constructs were evaluated during this study. For brevity, a sampling of the main results is shown in Table 1 (with OSF=0). In general, the purely probabilistic decision-making models performed poorly, and are not shown here. In all tables, results are based averages/percentages across all patients (n=500) in each construct simulation. As defined above, the goal here (i.e. optimality) is defined as maximizing patient improvement while minimizing treatment costs, which equates to minimizing CPUC. Additionally, generally we would prefer models that maintain reasonably high average final delta values and lower standard deviations of delta values.

Table 1 shows the results of the Hard Stop (i.e. case rate) and the Raw Effect (i.e. fee-for-service) decision models first. It should be noted that—for the former—CPUC is reduced but still generally higher than other decision making approaches while outcomes are very low, and that—for the latter—outcomes are improved but still generally lower than other decision making approaches while CPUC is significantly higher. In short, neither is optimal.

These more sophisticated AI decision-making approaches are superior to the aforementioned, more simplistic methods that are commonly employed in many healthcare payment methodologies (case rate, fee-for-service). An MDP model using a global transition model obtained higher outcomes than the Raw Effect (i.e. fee-for-service) model at significantly lower CPUC ($189 vs. $497), even in the face of missing observations.

It should also be noted that the same values in Table 1 were calculated for the broader patient population from an EHR system in an exemplary embodiment (such EHR system operating for a healthcare service provider with a fee-for-service payment model). These "treatment-as-usual" averages were estimated as: CPUC $540, final CDOI-ORS delta 4.4±9.5, and number of services 7.1. These real-world values roughly approximate the simulated values for the

TABLE 1

Model simulation results.

| Decision model | Transition model | Missing obs[a] | CPUC[b] | Avg final delta[c] | Std dev final delta[c] | Avg # of services | % Patients Max Dosage[d] |
|---|---|---|---|---|---|---|---|
| Hard Stop | N/A | No | 262.30 | 3.22 | 7.80 | 3.00 | 0% |
| Hard Stop | N/A | Yes | 305.53 | 2.56 | 8.07 | 3.00 | 0% |
| Raw Effect | 0th order | No | 470.33 | 4.69 | 8.66 | 8.00 | 100% |
| Raw Effect | 0th order | Yes | 497.00 | 4.73 | 8.45 | 8.00 | 100% |
| Max Improve | 1st order | No | 297.47 | 6.24 | 7.87 | 5.35 | 30% |
| Max Improve | 1st order | Yes | 303.85 | 5.77 | 8.25 | 5.32 | 29% |
| MDP | 1st order | No | 228.91 | 5.85 | 7.12 | 4.11 | 4% |
| MDP | 1st order | Yes | 237.21 | 5.11 | 7.37 | 4.03 | 3% |
| Max Improve | Global | No | 256.44 | 6.41 | 6.92 | 4.79 | 24% |
| Max Improve | Global | Yes | 251.83 | 6.07 | 6.90 | 4.76 | 20% |
| MDP | Global | No | 181.72 | 6.07 | 6.42 | 4.23 | 11% |
| MDP | Global | Yes | 189.93 | 5.59 | 6.44 | 4.11 | 9% |

[a]Missing observation.
[b]Cost per unit change.
[c]Final delta = change in outcome from baseline to end of treatment.
[d]Percent of patients receiving maximum number of treatment sessions.

More sophisticated decision-making models—including the Max Improve and the MDP models—performed much more optimally across various constructs. This included constructs with the inclusion of missing observations, which is a realistic challenge faced by any healthcare decision-maker. Generally speaking, the MDP decision-making models outperformed the Max Improve models in terms of minimizing CPUC, which was the primary metric of interest. However, the MDP approach generally achieved slightly lower outcome deltas, given an OSF=O. The MDP models did have slightly lower standard deviations for outcome deltas across patients except for a few constructs. In general, the MDP models appeared to be more consistent in tennis of our definition of optimality. We can also see that performance increases as we move from the 1st order to global transition models.

Raw Effect decision-making model, providing some ground validity for the simulation approach.

Since the MDP decision-making approaches consider utilities inherently as part of their decision-making approach, they provide additional opportunities for model refinement over other approaches, such as the simpler Max Improve model. One way to refine the model is by adjusting the outcome scaling factor. The results of such adjustment for the MDP model (using the global transition model and inclusion of missing observations) are shown in Table 2. Additionally, we ran the same experiment on a variation of the MDP model which takes the action with maximum probability (MaxProb) at each chance node, rather than the average/expected values. This is shown in Table 3.

TABLE 2

Outcome scaling-normal MDP.

| Outcome Scaling Factor | Decision model | Transition model | Missing obs[a] | CPUC[b] | Avg final delta[c] | Std dev final delta[c] | Avg # of services | % Patients Max Dosage[d] |
|---|---|---|---|---|---|---|---|---|
| 0 | MDP | Global | Yes | 189.93 | 5.59 | 6.44 | 4.112 | 9% |
| 1 | MDP | Global | Yes | 216.54 | 5.71 | 6.58 | 4.32 | 12% |
| 2 | MDP | Global | Yes | 219.95 | 6.17 | 6.58 | 4.62 | 14% |
| 3 | MDP | Global | Yes | 223.74 | 6.24 | 6.63 | 4.68 | 16% |
| 4 | MDP | Global | Yes | 235.87 | 6.26 | 6.62 | 4.70 | 16% |
| 5 | MDP | Global | Yes | 236.99 | 6.32 | 6.63 | 4.76 | 18% |

TABLE 2-continued

Outcome scaling-normal MDP.

| Outcome Scaling Factor | Decision model | Transition model | Missing obs[a] | CPUC[b] | Avg final delta[c] | Std dev final delta[c] | Avg # of services | % Patients Max Dosage[d] |
|---|---|---|---|---|---|---|---|---|
| 6 | MDP | Global | Yes | 243.87 | 6.29 | 6.80 | 4.80 | 19% |
| 10 | MDP | Global | Yes | 249.03 | 6.35 | 6.90 | 4.92 | 21% |

[a]Missing observation.
[b]Cost per unit change.
[c]Final delta = change in outcome from baseline to end of treatment.
[d]Percent of patients receiving maximum number of treatment sessions.

TABLE 3

Outcome scaling-MaxProb MDP.

| Outcome Scaling Factor | Decision model | Transition model | Missing obs[a] | CPUC[b] | Avg final delta[c] | Std dev final delta[c] | Avg # of services | % Patients Max Dosage[d] |
|---|---|---|---|---|---|---|---|---|
| 0 | MDP-MaxProb | Global | Yes | 219.75 | 6.35 | 6.60 | 4.73 | 14% |
| 1 | MDP-MaxProb | Global | Yes | 223.44 | 6.33 | 6.62 | 4.74 | 16% |
| 2 | MDP-MaxProb | Global | Yes | 222.11 | 6.36 | 6.61 | 4.76 | 17% |
| 3 | MDP-MaxProb | Global | Yes | 223.48 | 6.35 | 6.62 | 4.76 | 17% |
| 4 | MDP-MaxProb | Global | Yes | 235.56 | 6.35 | 6.62 | 4.76 | 17% |
| 5 | MDP-MaxProb | Global | Yes | 236.56 | 6.35 | 6.63 | 4.77 | 18% |
| 6 | MDP-MaxProb | Global | Yes | 239.28 | 6.32 | 6.66 | 4.78 | 19% |
| 10 | MDP-MaxProb | Global | Yes | 240.64 | 6.30 | 6.73 | 4.79 | 19% |

[a]Missing observation.
[b]Cost per unit change.
[c]Final delta = change in outcome from baseline to end of treatment.
[d]Percent of patients receiving maximum number of treatment sessions.

Figures 6A, 6B:
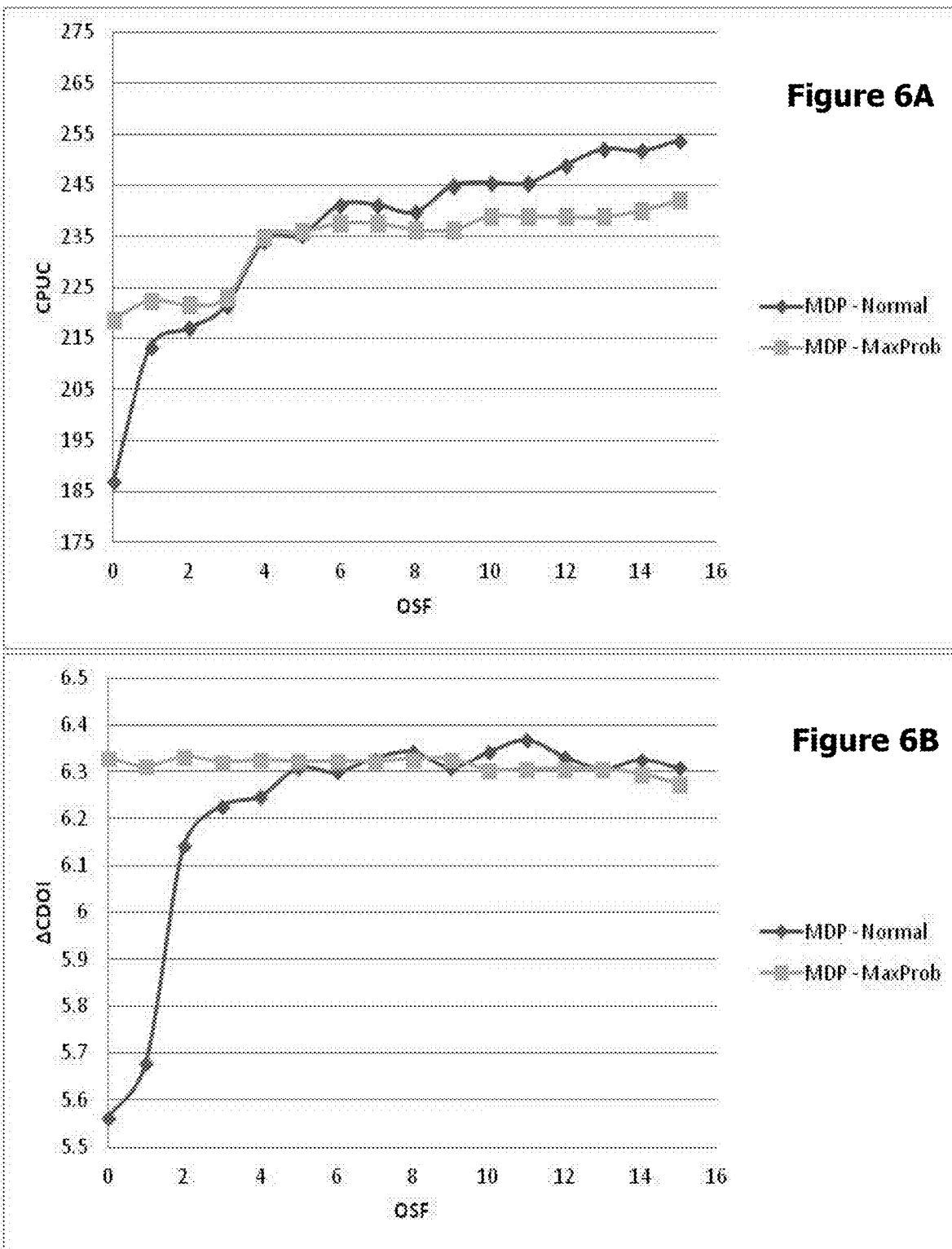
FIGS. 6A and 6B are graph diagrams showing relative cost per unit change comparisons involving embodiments of the present invention.

In Table 2, we can see that adjusting the OSF from 0 to 10 results in increasing outcome deltas, as well as increasing CPUC's. For the normal MDP, we appear to reach some sort of maxima in outcomes around OSF=3 or 4 (which is reflected in the MaxProb MDP below). After this, CPUC continues to rise, but outcome deltas show minimal improvement, even at OSF=10 and beyond. Effects on CPUC and outcome delta for both models using OSF ranging may be seen in the graphs of FIGS. 6A and 6B. FIGS. 6A and 6B show the effect of different values of the OSF parameter on CPUC (top) and outcome delta, i.e. ACDOI (bottom), for both the MDP-Normal and MDP-MaxProb Models. The delta values level off around 6.25-6.35 while CPUC values continue to increase.

We may see in table 3 that the MaxProb MDP show little change across OSF values in terms of CPUC or outcome deltas. This is probably evidence of some global maxima for CPUC $220-225 and outcome delta 6.25-6.35. Existence of such maxima should be expected given the optimization-problem nature of the current framework. It does suggest that such problems may be ripe for application of other optimization techniques for determining model parameters such as OSF or action/treatment decision thresholds.

It should be noted that with OSF=3, the normal MDP obtains CPUC=$224 and outcome delta=6.24 in 4.68 treatment sessions. This appears to be an optimal decision-making model across all model formulations given both CPUC and outcome deltas. It also vastly outperforms the aforementioned treatment-as-usual case rate/fee-for-service models (see Section 3.1). Essentially, we can obtain approximately 50% more improvement (outcome change) for roughly half the costs.

Embodiments of the present invention provide a general purpose (non-disease-specific) computational/AI framework that address fundamental healthcare challenges—rising costs, sub-optimal quality, difficulty moving research evidence into practice, among others. This framework serves at least two purposes: (1) A simulation environment for exploring various healthcare policies, payment methodologies, etc.; and (2) The basis for clinical artificial intelligence—an AI that can "think like a doctor"

This framework utilizes modern computational approaches to learn from clinical data and develop complex plans via simulation of numerous, alternative sequential decision paths. It determines optimal actions based on what has been observed so far, the beliefs inferred from those observations, and what we expect might happen in the future. It must do so in a dynamic environment as an online agent—which continually plans, observes, and re-plans over time as evidence/facts change. The framework is structured as a multi-agent system, which may additionally account for the various conflicting and synergistic interactions of various components in the healthcare system.

The results shown here demonstrate the feasibility of such an approach relative to human decision-making performance. Even in these exemplary embodiments, such an AI framework easily outperforms the current treatment-as-usual case-rate/fee-for-service models of healthcare. Sophisticated modeling approaches utilizing MDPs and DDNs may be further tweaked to provide finer control over the utility input of higher outcomes or lower costs depending on a particular embodiment's underlying policies and procedures, providing robust tools for simulation and AI development in the medical domain.

In addition to the embodiments disclosed above, such embodiments may be extended to the following within the framework of the present invention: (1) embodiments of agents having Personalized transition models—the integration of machine learning algorithms for optimal treatment selection for each patient; (2) Natural history of disease progression—For patients who receive no treatment as an action, further embodiments of personal agents may consider natural history rather than assuming they remain stable; (3) Variable physician agents—Vary behavior/decision-making by physician depending on individual physician priors (e.g., variable perceptions of outcome significance); (4) Variable patient agents—Consider variable patient behaviors (e.g. non-adherence to treatment, not taking medications, missing appointments); (5) Optimization methods for thresholds—The determination cutoffs of decision points between actions, rather than a priori determination via statistical methods. Agent may then determine such cut-points "on the fly."; (6) Gaussian noise for activity effects—further embodiments having realistic modeling of transitions between health states.; (7) Improved non-deterministic choices—For example, Monte Carlo simulations, rather than simply picking the max probability or random number, which in certain embodiments may yield better results; (8) Enhanced state conceptualization—embodiments where a combined global/local (1st order) delta state space is employed to capture both overall patient progress as well as short-term trajectories; and (9) Enhanced utility conceptualization—embodiments having alternative ways to estimate utility of a given action (e.g. different methods for weighting costs and outcomes).

For example, given the multi-agent design, the system may be modeled on an individual, personalized treatment basis (including genetics), i.e. "personalized medicine." Previously, we have described using machine learning methods to determine optimal treatments at a single timepoint for individual patients in references 7 and 9. Such methods may be combined into the sequential decision AI framework described here, simply by incorporating the output probabilities of those single-decision point treatment models into the transition models used by the sequential decision-making approaches. As such, each patient agent may thus maintain their own individualized transition model, which may then be passed into the physician agent at the time of decision-making for each patient. This is a significant advantage over a "one-size-fits-all" approach to healthcare, both in terms of quality as well as efficiency.

Quality and performance information may be incorporated into such models and may then be used as the basis for clinician reimbursement and/or clinical decision-making (e.g. pay-for-performance), again depending on the policies and procedures of the institution implementing a new embodiment.

Other opportunities include considering combinations of global/local (1st order) deltas to capture both long-term prognosis as well as short-term trajectories, modeling variable patient behaviors (e.g. non-adherence to medications), testing alternative utility metrics, and utilizing optimization techniques to determine decision cutoff thresholds between actions on-the-fly. Each such type of study may indicate further areas to modify and enhance the general methodologies described above and within the parameters of the present invention.

If we more reliably predict the likely result of a sequence of actions/treatment for some time out into the future, we may use that to determine the optimal action right now. As recently pointed out by the Institute of Medicine, does it make sense to continue to have human clinicians attempt to estimate the probabilistic effects of multiple actions over time, across multitudes of treatment options and variable patient characteristics, in order to derive some intuition of the optimal course of action? Or would we be better served to free them to focus on delivery of actual patient care? Embodiments of the present invention add to a growing body of evidence that such complex treatment decisions may be better handled through modeling than intuition alone. Furthermore, the potential exists to extend this framework as a technical infrastructure for delivering personalized medicine. Such an approach presents real opportunities to address the fundamental healthcare challenges of our time, and may serve a critical role in advancing human performance as well.

The following references were used in the development of the present invention, and the disclosures of which are explicitly incorporated by reference herein:

[1] V. L. Patel, E. H. Shortliffe, M. Stefanelli, P. Szolovits, M. R. Berthold, R. Bellazzi, et al., The Coming of Age of Artificial Intelligence in Medicine, Artif Intell Med, (2009) 46(1): 5-17.

[2] E. A. McGlynn, S. M. Asch, J. Adams, J. Keesey, J. Hicks, A. DeCristofaro A, et al., The quality of health care delivered to adults in the United States, N Engl J Med, (2003) 348(26): 2635-2645

[3] M. S. Bauer, A review of quantitative studies of adherence to mental health clinical practices guidelines, Hary Rev Psychiatry, (2002) 10(3): 138-153.

[4] B. Kaplan, Evaluating informatics applications—clinical decision support systems literature review, Int J Med Inform, (2001) 64(1): 15-37.

[5] P. R. Orszag and P. Ellis, The challenge of rising health care costs—a view from the Congressional Budget Office, N Engl J Med, (2007) 357(18): 1793-1795.

[6] G. P. Jackson and J. L. Tarpley, How long does it take to train a surgeon? BMJ, (2009) 339: b4260-b4260.

[7] C. C. Bennett and T. W. Doub, Data mining and electronic health records: Selecting optimal clinical treatments in practice, Proceedings of the 6th International Conference on Data Mining, (CSREA Press, Las Vegas, Nev., 2010) 313-318. http://arxiv.orgiabs/1112.1668 (Accessed: 11 May 2012).

[8] J. A. Osheroff, J. M. Teich, B. Middleton, E. B. Steen, A. Wright, and D. E. Detmer. A roadmap for national action on clinical decision support, J Am Med Inform Assoc, (2007) 14(2):141-145.

[9] C. C. Bennett, T. W. Doub, A. D. Bragg, J. Luellen, C. Van Regenmorter, J. Lockman, et al., Data Mining Session-Based Patient Reported Outcomes (PROs) in a Mental Health Setting: Toward Data-Driven Clinical Decision Support and Personalized Treatment, IEEE Health Informatics, Imaging, and Systems Biology Conference, (IEEE, San Jose, Calif., 2011) 229-236. http://arxiv.org/abs/1112.1670 (Accessed: 11 May 2012).

[10] I. S. Kohane, The twin questions of personalized medicine: who are you and whom do you most resemble? Genome Med, (2009) 1(1): 4.

[11] Y. Sun Y, S. Goodison S, J. Li, L. Liu, and W. Farmerie, Improved breast cancer prognosis through the combination of clinical and genetic markers, Bioinformatics, (2007) 23(1): 30-37.

[12] 0. Gevaert, F. De Smet, D. Timmerman, Y. Moreau, and B, De Moor, Predicting the prognosis of breast cancer by integrating clinical and microarray data with Bayesian networks, Bioinformatics, (2006) 22(14):184-190.

[13] A. L. Boulesteix, C. Porzelius, and M. Daumer, Microarray-based classification and clinical predictors: on combined classifiers and additional predictive value, Bioinformatics, (2008) 24(15): 1698-1706.

[14] J. R. Beck and S. G. Pauker, The Markov process in medical prognosis, Med Decis Making, (1983) 3(4):419-58.

[15] Y. Xiang and K. L. Poh, Time-critical dynamic decision modeling in medicine, Comput Biol Med, (2002) 32(2): 85-97.

[16] T. Y. Leong, Dynamic decision modeling in medicine: a critique of existing formalisms., Proc Annu Symp Comput Appl Med Care, (AMIA, Washington, D.C., 1993) 478-484.

[17] J. E. Stahl, Modelling methods for pharmacoeconomics and health technology assessment: an overview and guide, Pharmacoeconomics, (2008) 26(2): 131-48.

[18] A. J. Schaefer, M. D. Bailey, S. M. Shechter, and M. S. Roberts, Modeling Medical Treatment Using Markov Decision Processes, in: M. L. Brandeau, F. Sainfort, and W. P. Pierskalla, eds., Operations Research and Health Care, (Kluwer Academic Publishers, Boston, 2005) 593-612.

[1910. Alagoz, H. Hsu, A. J. Schaefer, and M. S. Roberts, Markov Decision Processes: A Tool for Sequential Decision Making under Uncertainty, Med Decis Making, (2010) 30(4): 474-83.

[20] S. M. Shechter, M. D. Bailey, A. J. Schaefer, and M. S. Roberts, The Optimal Time to Initiate HIV Therapy Under Ordered Health States, Oper Res, (2008) 56(1): 2033.

[21] P. E. Meehl, Causes and effects of my disturbing little book, Journal of Personality Assessment, (1986) 50(3): 370-375.

[22] V. L. Patel, J. F. Arocha, and D. R. Kaufman, A Primer on Aspects of Cognition for Medical Informatics, J Am Med Inform Assoc, (2001) 8(4): 324-43.

[231 A. S. Elstein and A. Schwarz, Clinical problem solving and diagnostic decision making: selective review of the cognitive literature, BMJ, (2002) 324(7339): 729-32.

[24] M. L. Littman, A tutorial on partially observable Markov decision processes, J Math Psychol, (2009) 53(3): 119-25.

[25] S. Russell and P. Norvig, Artificial Intelligence: A Modern Approach, 3rd Ed, (Prentice Hall, Upper Saddle River, N J, 2010).

[26] Y. Gocgun, B. W. Bresnahan, A. Ghate, and M. L. Gunn, A Markov decision process approach to multi-category patient scheduling in a diagnostic facility, Artif Intell Med, (2011) 53(2): 73-81.

[27] F. Bousquet and C. Le Page, Multi-agent simulations and ecosystem management: a review, Ecol Modell, (2004) 176(3-4): 313-32.

[28] S. D. Miller, B. L. Duncan, J. Brown, R. Sorrell, and M. B. Chalk, Using formal client feedback to improve retention and outcome: Making ongoing, real-time assessment feasible, Journal of Brief Therapy, (2006) 5(1): 5-22.

[29] A. Campbell and S. Hemsley, Outcome Rating Scale and Session Rating Scale in psychological practice: Clinical utility of ultra-brief measures, Clinical Psychologist, (2009) 13(1): 1-9.

[30] C. C. Bennett, Clinical Productivity System: A Decision Support Model, International Journal of Productivity and Performance Management, (2010) 60(3): 311319.

[311 J. Kreke, M. D. Bailey, A. J. Schaefer, D. Angus, and M. S. Roberts, Modeling hospital discharge policies for patients with pneumonia-related sepsis, IIE Transactions, (2008) 40(9): 853-860.

[32] J. E. Goulionis and A. Vozikis, Medical decision making for patients with Parkinson disease under average cost criterion, Aust New Zealand Health Policy, (2009) 6: 15.

[33] S. Ross, J. Pineau, S. Paquet, and B. Chaib-draa, Online planning algorithms for POMDPs. J Artif Intell Res, (2008) 32:663-704.

[34] M. Hauskrecht and H. Fraser, Planning treatment of ischemic heart disease with partially observable Markov decision processes, Artif Intell Med, (2000) 18(3): 22144.

[351 T. Hester and P. Stone, An Empirical Comparison of Abstraction in Models of Markov Decision Processes, Proceedings of the ICML/UAI/COLT Workshop on Abstraction in Reinforcement Learning, (ICML, Montreal, Canada, 2009) 18-23.

[36] M. Kim, A. Ghate, and M. H. Phillips, A Markov decision process approach to temporal modulation of dose fractions in radiation therapy planning, Phys Med Biol, (2009) 54(14): 4455-4476.

[37] M. Brown, E. Bowring, S. Epstein, M. Jhaveri, R. Maheswaran, P. Mallick, et al, Applying Multi-Agent Techniques to Cancer Modeling, Proceedings of the 6th Annual Workshop on Multiagent Sequential Decision Making in Uncertain Domains (MSDM), (AAMAS, Taipei, Taiwan, 2011) 8-15.

[38] M. B. Rosenthal, Beyond Pay for Performance—Emerging Models of Provider-Payment Reform, N Engl J Med, (2008) 359(12): 1197-1200.

[39] Institute of Medicine, Informing the Future: Critical Issues in Health, 6th Edition, (The National Academies Press, Washington, D.C., 2011).

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method of providing decision support for assisting medical treatment decision-making, comprising:
   receiving, by a health care computing device and from a first device operating an agent software module, evidence based information corresponding to a health status of a particular patient and patient treatment decisions;
   filtering, by the health care computing device, the evidence based information to create a plurality of decision-outcome nodes comprising a plurality of belief state nodes reflecting potential future effects of different treatment choices;
   determining an optimal treatment for the particular patient by evaluating the plurality of decision-outcome nodes with a scoring function, wherein the scoring function comprises a cost per unit change function and includes calculating the cost in an amount it takes to obtain one unit of outcome change (delta) on a given outcome;
   transmitting, by the health care computing device and to the first device, one or more first messages describing the determined optimal treatment;
   receiving, by the health care computing device, observation data corresponding to the particular patient after the patient was physically administered the determined optimal treatment;
   updating at least one of the plurality of belief state nodes using the received observation data;
   determining a new optimal treatment for the particular patient by evaluating the updated plurality of decision-outcome nodes with the scoring function; and transmitting, by the health care computing device and to the first device, one or more second messages describing the determined new optimal treatment.

2. The method of claim 1 wherein the calculation involves the following equation:

$$\pi^* = \arg\min_{\pi} CPUC(\pi)$$

$$= \arg\min_{\pi} E \begin{cases} \dfrac{C_T(\pi)}{\Delta CDOI(\pi)}, & \text{if } \Delta CDOI(\pi) \geq 1 \\ \dfrac{C_T(\pi)}{1} + (1 - \Delta CDOI(\pi)) \times CPS, & \text{else} \end{cases}$$

where CPS=cost per service for a given session, CT is a random variable denoting accumulated cost at the end of treatment, E indicates expected value, and ACDOI (it) is calculated as:

$$\Delta CDOI(\pi) = CDOI_T(\pi) - CDOI_0$$

where $CDOI_T$ is a random variable denoting the CDOI-ORS value at the end of treatment.

3. The method of claim 1 wherein the evidence based information includes a plurality of health status information at a plurality of times.

4. The method of claim 1 wherein software creating the decision-outcome nodes includes a module that receives rewards/utilities, and a module to select patient treatments in order to maximize overall utilities.

5. The method of claim 1 wherein the decision-outcome nodes are updated according to a transition model.

6. The method of claim 1 the plurality of decision-output nodes are configured as a multi-level tree.

7. The method of claim 1 wherein the evidence based information includes at least one of clinical data, electronic health record information, and genetic data.

8. The method of claim 1 wherein upon receiving additional evidence based information, each of the decision-output nodes are recalculated.

9. A decision support system for assisting medical treatment decision-making, said system comprising:
a processor and associated memory, said memory including program memory configured to store instructions for enabling said processor to perform operations, and said memory including storage memory configured to store data upon which said processor performs operations;
said storage memory including data relating to a particular patient;
said program memory including a plurality of instructions that when executed by said processor enables said process to execute the following steps:
receive, from a first device operating a patient agent software module, information about a particular patient;
receive, from a second device operating a doctor agent software module, information about a health status of the particular patient, doctor beliefs relating to at least one of patient treatments and treatment effects, and evidence based information relating to effects of patient treatments;
filter the information from the patient agent and the information from the doctor agent to create a plurality of decision-outcome nodes comprising a plurality of belief state nodes reflecting potential future effects of different treatment choices;
create a patient-specific outcome based on the plurality of decision-outcome nodes;
determine an optimal treatment by evaluating the plurality of decision-outcome nodes with a scoring function and outputting the optimal treatment, wherein the scoring function comprises a cost per unit change function and includes calculating the cost in an amount it takes to obtain one unit of outcome change (delta) on a given outcome;
cause transmission of one or more first messages describing the determined optimal treatment;
receive observation data corresponding to the particular patient after the patient was physically administered the determined optimal treatment;
update at least one of the plurality of belief state nodes using the received observation data;
determine a new optimal treatment for the particular patient by evaluating the updated plurality of decision-outcome nodes with the scoring function; and
cause transmission of one or more second messages describing the determined new optimal treatment.

10. The decision support system of claim 9 wherein the calculation involves the following equation:

$$\pi^* = \arg\min_{\pi} CPUC(\pi)$$

$$= \arg\min_{\pi} E \begin{cases} \dfrac{C_T(\pi)}{\Delta CDOI(\pi)}, & \text{if } \Delta CDOI(\pi) \geq 1 \\ \dfrac{C_T(\pi)}{1} + (1 - \Delta CDOI(\pi)) \times CPS, & \text{else} \end{cases}$$

where CPS=cost per service for a given session, CT is a random variable denoting accumulated cost at the end of treatment, E indicates expected value, and ACDOI (it) is calculated as:

$$\Delta CDOI(\pi) = CDOI_T(\pi) - CDOI_0$$

where $CDOI_T$ is a random variable denoting the CDOI-ORS value at the end of treatment.

11. The decision support system of claim 9 wherein the patient agent includes a plurality of health status information at a plurality of times.

12. The decision support system of claim 9 wherein the doctor agent includes a module that receives rewards/utilities, and a module to select patient treatments in order to maximize overall utilities.

13. The decision support system of claim 9 wherein the decision-outcome nodes are updated according to a transition model.

14. The decision support system of claim 9 further including a learning software module with a knowledge base wherein when additional information is available, such information is included in the knowledge base used by at least one of the patient agent software module, the doctor agent software module, and the determining optimal treatment step.

15. The decision support system of claim 9 the doctor agent software has evidence based information from at least one of clinical information, electronic health record information, and genetic information.

16. The decision support system of claim 9 wherein said plurality of decision-outcome nodes are configured as a multi-level tree.

17. A server for providing decision support for medical treatment decision-making, said system comprising:

a processor and associated memory, said memory including program memory configured to store instructions for enabling said processor to perform operations, and said memory including storage memory configured to store data upon which said processor performs operations;

said storage memory including data relating to a particular patient;

said program memory including a plurality of instructions that when executed by said processor enables said processor to execute the following steps:

receive, from a first device, evidence based information about a health status of the particular patient, doctor beliefs relating to at least one of patient treatments and treatment effects, and patient treatment decisions;

filter the evidence based information to create a plurality of decision-outcome nodes comprising a plurality of belief state nodes reflecting potential future effects of different treatment choices;

determine an optimal treatment by evaluating the plurality of decision-outcome nodes with a scoring function and outputting the optimal treatment, wherein the scoring function comprises a cost per unit change function and includes calculating the cost in an amount it takes to obtain one unit of outcome change (delta) on a given outcome;

cause transmission of one or more first messages describing the determined optimal treatment;

receive observation data corresponding to the particular patient after the patient was physically administered the determined optimal treatment;

update at least one of the plurality of belief state nodes using the received observation data;

determine a new optimal treatment for the particular patient by evaluating the updated plurality of decision-outcome nodes with the scoring function; and cause transmission of one or more second messages describing the determined new optimal treatment.

* * * * *